(12) United States Patent
Shultz et al.

(10) Patent No.: US 9,186,256 B2
(45) Date of Patent: Nov. 17, 2015

(54) WRIST IMPLANTS AND METHODS

(75) Inventors: Jason Shultz, Liberty Township, OH (US); Brian Adams, Iowa City, IA (US)

(73) Assignee: Integra LifeSciences Corporation, Plainsboro, NJ (US)

( * ) Notice: Subject to any disclaimer, the term of this patent is extended or adjusted under 35 U.S.C. 154(b) by 0 days.

(21) Appl. No.: 13/588,807

(22) Filed: Aug. 17, 2012

(65) Prior Publication Data

US 2013/0053974 A1 Feb. 28, 2013

Related U.S. Application Data

(60) Provisional application No. 61/525,449, filed on Aug. 19, 2011.

(51) Int. Cl.
*A61F 2/42* (2006.01)
*A61B 17/17* (2006.01)
*A61B 17/86* (2006.01)
*A61F 2/30* (2006.01)

(52) U.S. Cl.
CPC ........... *A61F 2/4261* (2013.01); *A61B 17/1739* (2013.01); *A61B 17/86* (2013.01); *A61B 2017/1782* (2013.01); *A61F 2002/30125* (2013.01); *A61F 2002/30327* (2013.01); *A61F 2002/30934* (2013.01); *A61F 2002/4264* (2013.01)

(58) Field of Classification Search
CPC ................ A61F 2/4261; A61F 2/4269; A61F 2002/4264; A61F 2002/4266; A61F 2002/4271; A61F 2002/4274–2002/4297
USPC ............................................ 623/21.11–21.14
See application file for complete search history.

(56) References Cited

U.S. PATENT DOCUMENTS

| 4,645,505 | A | * | 2/1987 | Swanson | ..................... 623/21.12 |
|---|---|---|---|---|---|
| 5,702,470 | A | | 12/1997 | Menon | |
| 6,059,832 | A | | 5/2000 | Menon | |
| 6,746,486 | B1 | | 6/2004 | Shultz | |
| 7,531,003 | B2 | | 5/2009 | Reindel | |
| 7,625,408 | B2 | | 12/2009 | Gupta | |
| 7,628,819 | B2 | | 12/2009 | Gupta | |

(Continued)

FOREIGN PATENT DOCUMENTS

EP  2559407  2/2013

OTHER PUBLICATIONS

European Search Report and Written Opinon for Application No. 12181020.4 dated Oct. 16, 2012.

(Continued)

*Primary Examiner* — Thomas J Sweet
*Assistant Examiner* — Brian Dukert
(74) *Attorney, Agent, or Firm* — Jenkins, Wilson, Taylor & Hunt, P.A.

(57) ABSTRACT

Wrists implants and methods are disclosed. A wrist implant can advantageously allow motion with respect to a reconstructed wrist to more closely resemble natural motion. For example, in one aspect, motion can include movement in more than one direction to allow for flexion/extension, rotational, and translational movement. The wrist implant can include a radial implant component and/or a carpal implant component with a bearing component or member disposed therebetween. The radial implant can have a radial articulation surface having at least one variable radius of curvature and/or a tray having a variable width.

12 Claims, 34 Drawing Sheets

(56) References Cited

U.S. PATENT DOCUMENTS

| | | |
|---|---|---|
| 7,766,970 B2 | 8/2010 | Shultz |
| 8,052,756 B2 | 11/2011 | Vanasse |
| 8,066,777 B2 | 11/2011 | Palmer |
| 8,105,388 B2 | 1/2012 | Palmer |
| 8,105,389 B2 | 1/2012 | Berelsman |
| 8,105,390 B2 | 1/2012 | Shultz |
| 8,118,876 B2 | 2/2012 | Gupta |
| 8,372,154 B2 | 2/2013 | Shultz |
| 2004/0117025 A1* | 6/2004 | Reindel ............... 623/18.11 |
| 2005/0085921 A1 | 4/2005 | Gupta et al. |
| 2007/0055381 A1 | 3/2007 | Berelsman |
| 2012/0078376 A1 | 3/2012 | Vanasse |
| 2012/0095565 A1 | 4/2012 | Shultz |
| 2012/0150308 A1 | 6/2012 | Gupta |

OTHER PUBLICATIONS

Extended European Search Report for Application No. 12181020.4 dated Feb. 19, 2013.

* cited by examiner

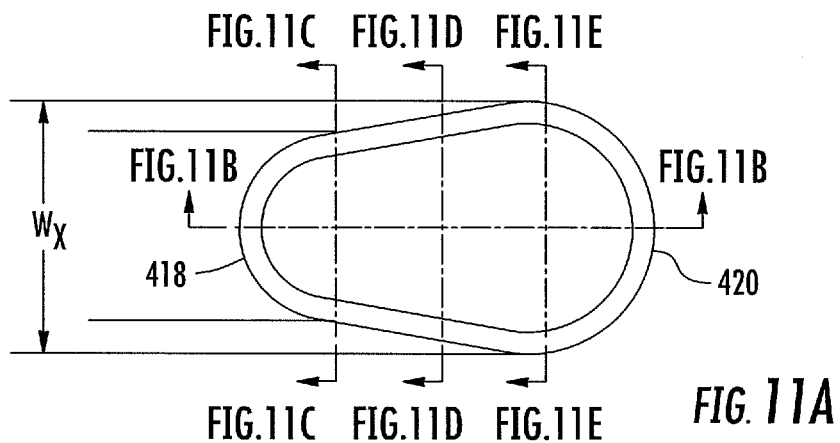
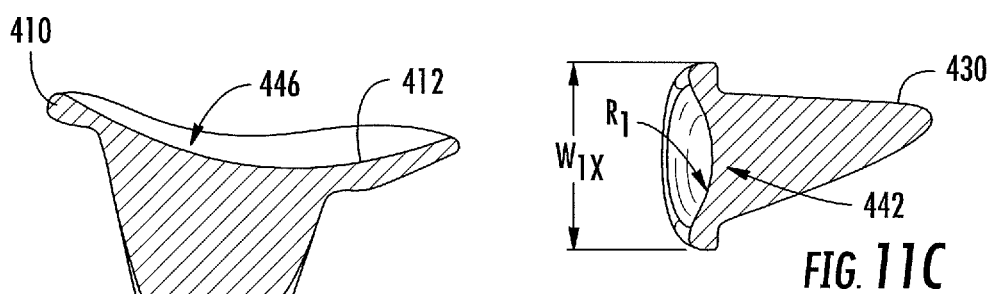
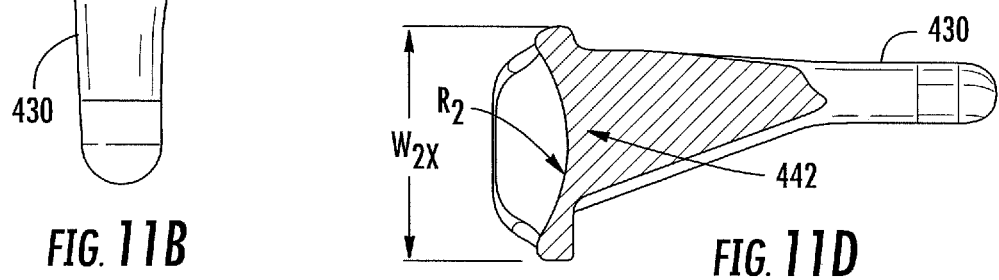
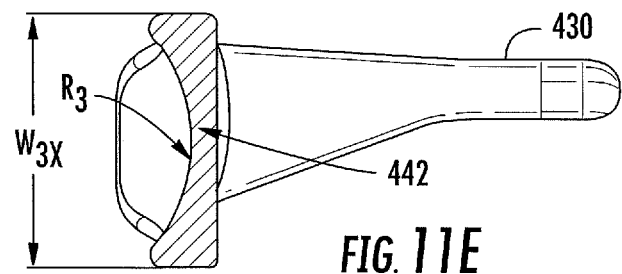
FIG. 11A
FIG. 11B
FIG. 11C
FIG. 11D
FIG. 11E

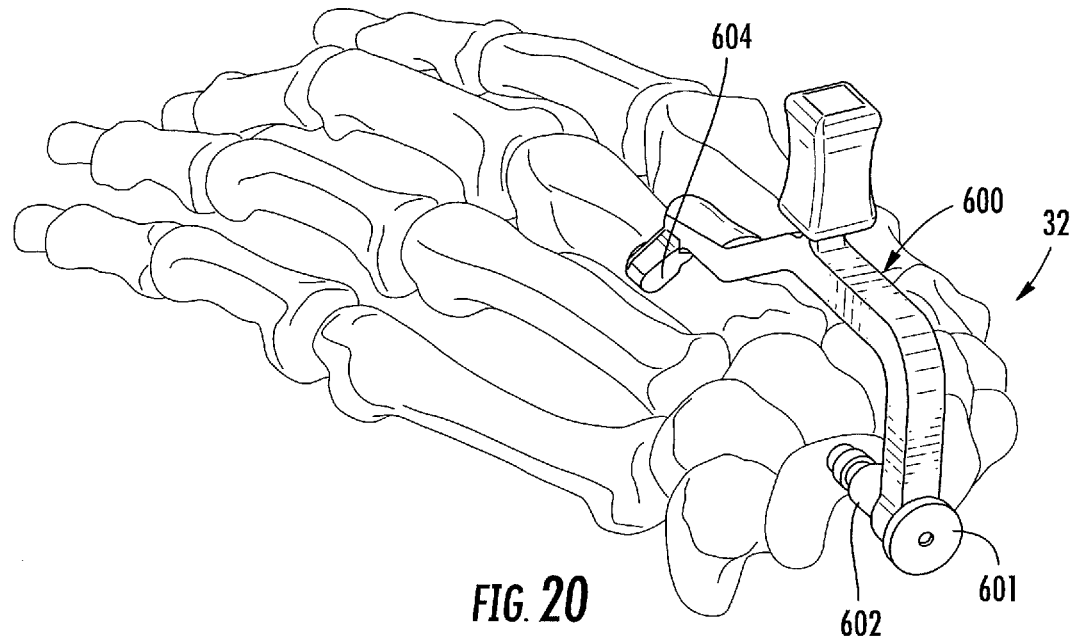
FIG. 20
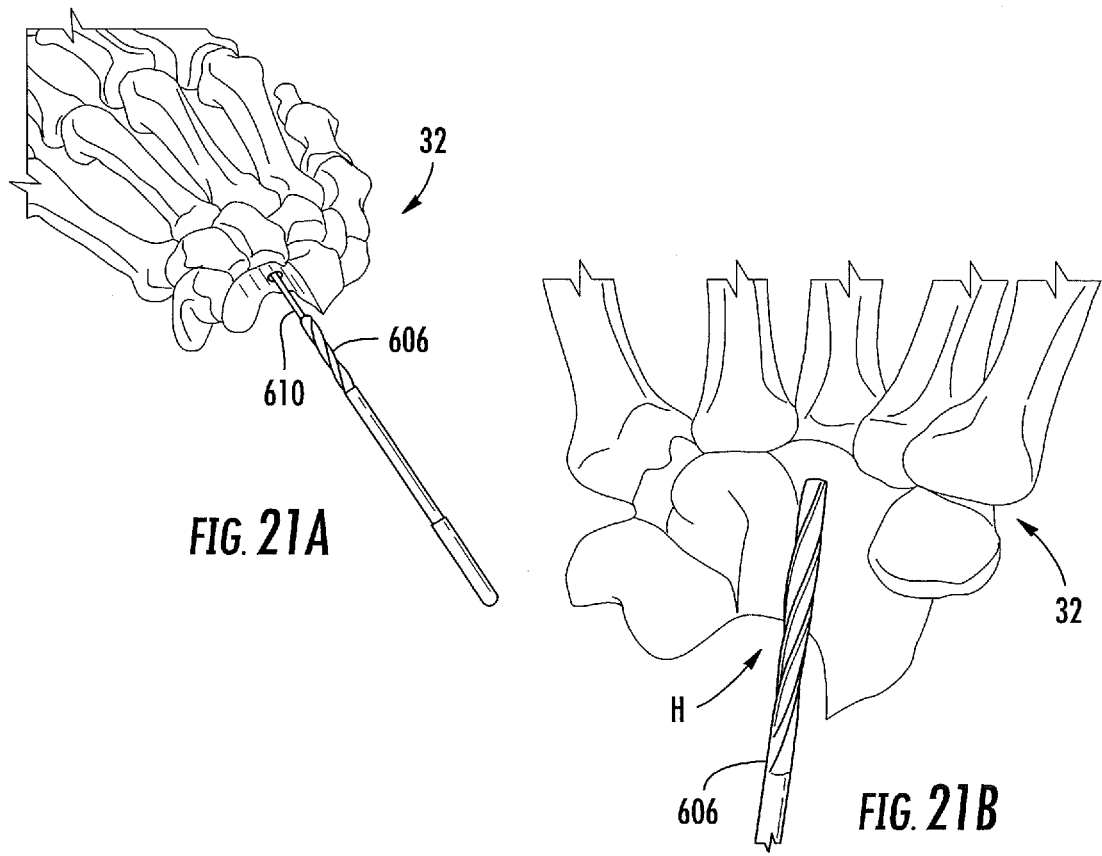
FIG. 21A
FIG. 21B

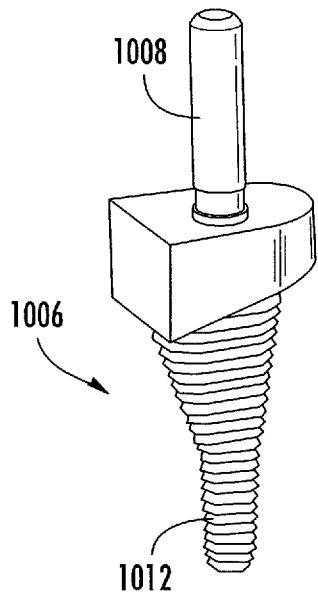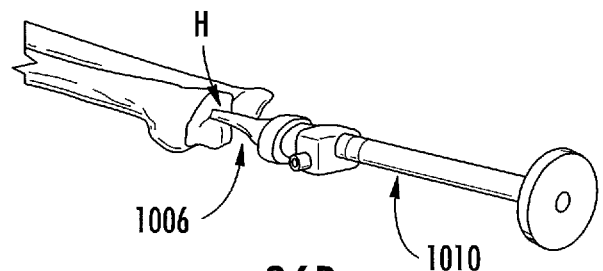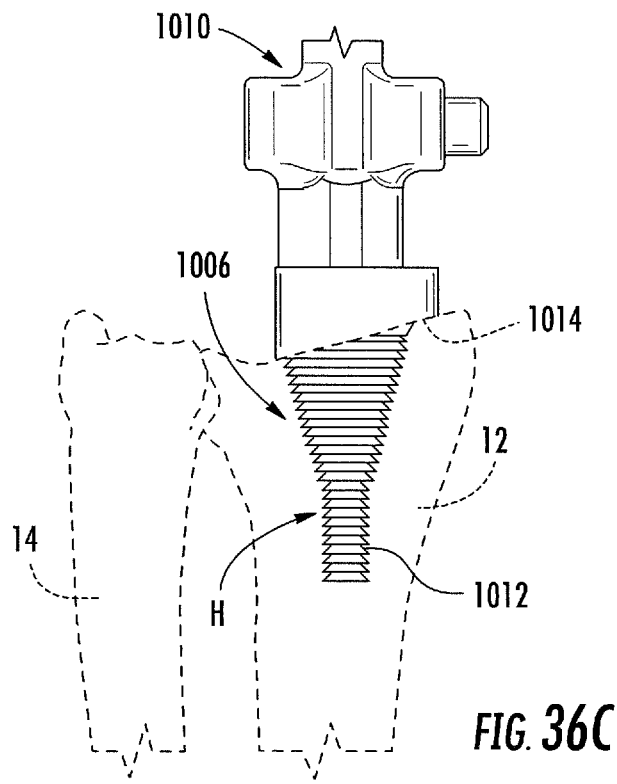
FIG. 36A
FIG. 36B
FIG. 36C

WRIST IMPLANTS AND METHODS

CROSS-REFERENCE TO RELATED APPLICATION

This application claims priority to provisional patent application U.S. Ser. No. 61/525,449 filed on Aug. 19, 2011.

TECHNICAL FIELD

The subject matter disclosed herein relates generally to prosthetic implants and related systems and methods for implantation. More specifically, the subject matter disclosed herein relates to total wrist arthroplasty and radial hemiarthroplasty systems and methods of using wrist implants for reconstruction of the wrist joint.

BACKGROUND

A wrist that has been damaged by an injury or has been affected by a disorder such as arthritis may produce pain and may not function properly. In severe cases, patients may suffer from severe wrist pain and can lose the ability to use the wrist. Previously, such severe wrist conditions that were unresponsive to other treatments were addressed with a procedure known as wrist arthrodesis. The procedure fuses the bones of the wrist together to reduce or eliminate pain. However, if the bones are fused together, movement of the wrist is severely limited or lost.

Total wrist replacement surgery, also known as total wrist arthroplasty, replaces the damaged wrist joint with a prosthetic wrist implant. Unlike wrist arthrodesis, a wrist replacement eliminates pain without compromising wrist movements. U.S. Pat. Nos. 5,702,470 and 6,059,832 describe a prosthetic wrist implant disposed between a patient's radius and carpal complex bones. The implant includes a radial implant component, a carpal bone implant component, and an articulating bearing member that is fastened to the carpal bone implant component and slidingly engages the radial implant component. The articulating bearing member of these patents can be designed to connect laterally (sideways from the dorsal plane) onto the carpal bone implant component through the use of slots on the bearing member that connect with tabs on the carpal bone implant component.

Alternatively, in patients with severe arthritis who do not qualify for total wrist arthroplasty but request an alternative to complete wrist fusion, a procedure called radial hemiarthroplasty can be used. In this procedure, only the radial component of a total wrist arthroplasty system can be used.

Although the existing prosthetic wrist implants can relieve pain without causing loss of wrist movement, it is desirable to provide improved prosthetic wrist implant components and systems having enhanced stability and a greater degree of movement or freedom in the joint.

SUMMARY

It is an object of the present disclosure to provide novel wrist implant components, systems, and methods, where the wrist implants can allow a reconstructed wrist to more closely resemble natural motion. It is another object of the present disclosure to provide wrist implant components and systems having improved initial stability and long term fixation. Wrist implant components can engage and/or connect to form wrist implant systems. Such systems can include both a carpal implant component and a radial implant component, or a carpal implant component or a radial implant component alone.

In one aspect of the present disclosure, wrist implant components and systems can be provided with a radial articulation surface having a variable radius of curvature or variable radius of articulation and/or a radial tray having a variable width. In other aspects of the present disclosure, wrist implant components and systems can include rotation of a radial tray with respect to a radial stem.

A few objects of the presently disclosed subject matter having been stated hereinabove, and which are achieved in whole or in part by the presently disclosed subject matter, other objects will become evident as the description proceeds when taken in connection with the accompanying drawings as best described hereinbelow.

BRIEF DESCRIPTION OF THE DRAWINGS

A full and enabling disclosure of the present subject matter including the best mode thereof to one of ordinary skill in the art is set forth more particularly in the remainder of the specification, including reference to the accompanying figures, in which:

FIG. 11 depicts sectional views illustrating a radial implant component;

FIGS. 18-45 illustrate a surgical technique of implanting the prosthetic wrist implant.

DETAILED DESCRIPTION

Figure 1:
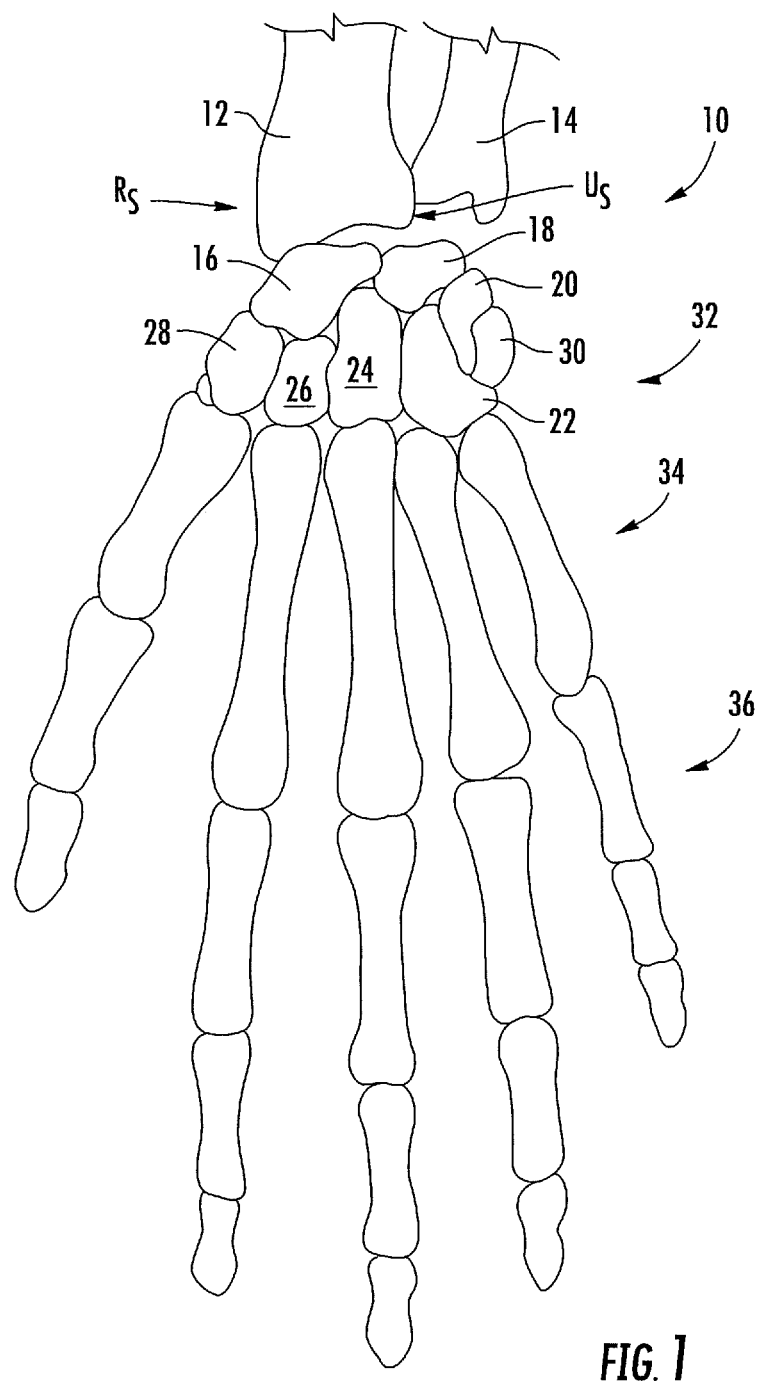
FIG. 1 is an illustration of the bones of the left hand on a dorsal side.

Reference will now be made in detail to the description of the present subject matter, one or more examples of which are shown in the figures. Each example is provided to explain the subject matter and not as a limitation. In fact, features illustrated or described as part of one embodiment can be used in another embodiment to yield still a further embodiment. It is intended that the present subject matter cover such modifications and variations.

As illustrated in the various figures, some sizes of structures or portions are exaggerated relative to other structures or portions for illustrative purposes and, thus, are provided to illustrate the general structures of the present subject matter. Furthermore, various aspects of the present subject matter are described with reference to a structure or a portion being formed on other structures, portions, or both. As will be appreciated by those of skill in the art, references to a structure being formed "on" or "above" another structure or portion contemplates that additional structure, portion, or both may intervene. References to a structure or a portion being formed "on" another structure or portion without an intervening structure or portion are described herein as being formed "directly on" the structure or portion. Similarly, it will be understood that when an element is referred to as being "connected", "attached", or "coupled" to another element, it can be directly connected, attached, or coupled to the other element, or intervening elements may be present. In contrast, when an element is referred to as being "directly connected", "directly attached", or "directly coupled" to another element, no intervening elements are present.

Furthermore, relative terms such as "on", "above", "upper", "top", "lower", or "bottom" are used herein to describe one structure's or portion's relationship to another structure or portion as illustrated in the figures. It will be understood that relative terms such as "on", "above", "upper", "top", "lower" or "bottom" are intended to encompass different orientations of the package or component in addition to the orientation depicted in the figures. For example, if the package or component in the figures is turned over, structure or portion described as "above" other structures or portions would now be oriented "below" the other structures or portions. Likewise, if the package or component in the figures are rotated along an axis, structure or portion described as "above", other structures or portions would be oriented "next to" or "left of the other structures or portions. Like numbers refer to like elements throughout.

Unless the absence of one or more elements is specifically recited, the terms "comprising", including", and "having" as used herein should be interpreted as open-ended terms that do not preclude the presence of one or more elements.

The wrist joint is a very complex joint, with the articulation of the eight carpal bones with the radius and among themselves resulting in complex motions. Attempting to replace this complex construct with a single articulation in a joint replacement has limitations. The present subject matter discloses prosthetic wrist implants comprising wrist components and/or wrist systems which can both improve implant stability and allow natural articulation of the hand. The wrist implant components and systems can utilize screws, bone cement, and/or press-fit properties for attachment to the carpal component, the radial component, or both, and provides a stable and strong attachment with minimal bone removal.

Referring now to FIG. 1, the bones of a left hand are shown viewing the dorsal side and/or include a dorsal view of portions of a radius 12 and an ulna 14. A volar side or volar view opposes this view. In particular, FIG. 1 shows the bones of the wrist 10 including radius 12, ulna 14, scaphoid 16, lunate 18, triquetrum 20, hamate 22, capitate 24, trapezoid 26, trapezium 28, and pisiform 30. Bones 16-30 make up the carpal bone complex 32 of the hand. Additional bones that will not be discussed in detail include the metacarpal bones 34 and the phalanges bones 36. It will be appreciated that the scaphoid 16 and lunate 18 bones articulate with radius 12 to provide motion of the wrist. Notably, components, systems, and methods disclosed herein can be configured to engage, communicate with, and/or replace at least one the bones of wrist 10 while simulating and/or maintaining bone articulation and/or bone movement within portions of wrist 10. In one aspect, a radial implant component can be disposed over portions of radius 12. The implant may be discussed with respect to an ulnar side as viewed along and/or proximate arrow $U_S$ and a radial side as viewed along and/or proximate arrow $R_S$.

Prosthetic wrist implant components and systems disclosed herein can comprise a radial implant component comprising a tray having a distal bearing surface and a proximal surface having an elongated radial stem extending therefrom adapted for fixation to radius 12. The tray can have radial and ulnar sides and volar and dorsal sides (dorsal side shown in FIG. 1, volar side would be the opposing view) and a carpal implant component comprising a carpal plate having a distal surface adapted for attachment to one or more carpal bones of complex 32 and a proximal surface adapted to couple with a bearing component or bearing member. The bearing member can have a proximal bearing surface for articulation with the distal bearing surface of the radial component. The proximal bearing surface of the bearing member can be at least substantially convex and the distal bearing surface of the radial component can be at least substantially concave.

Figure 5:
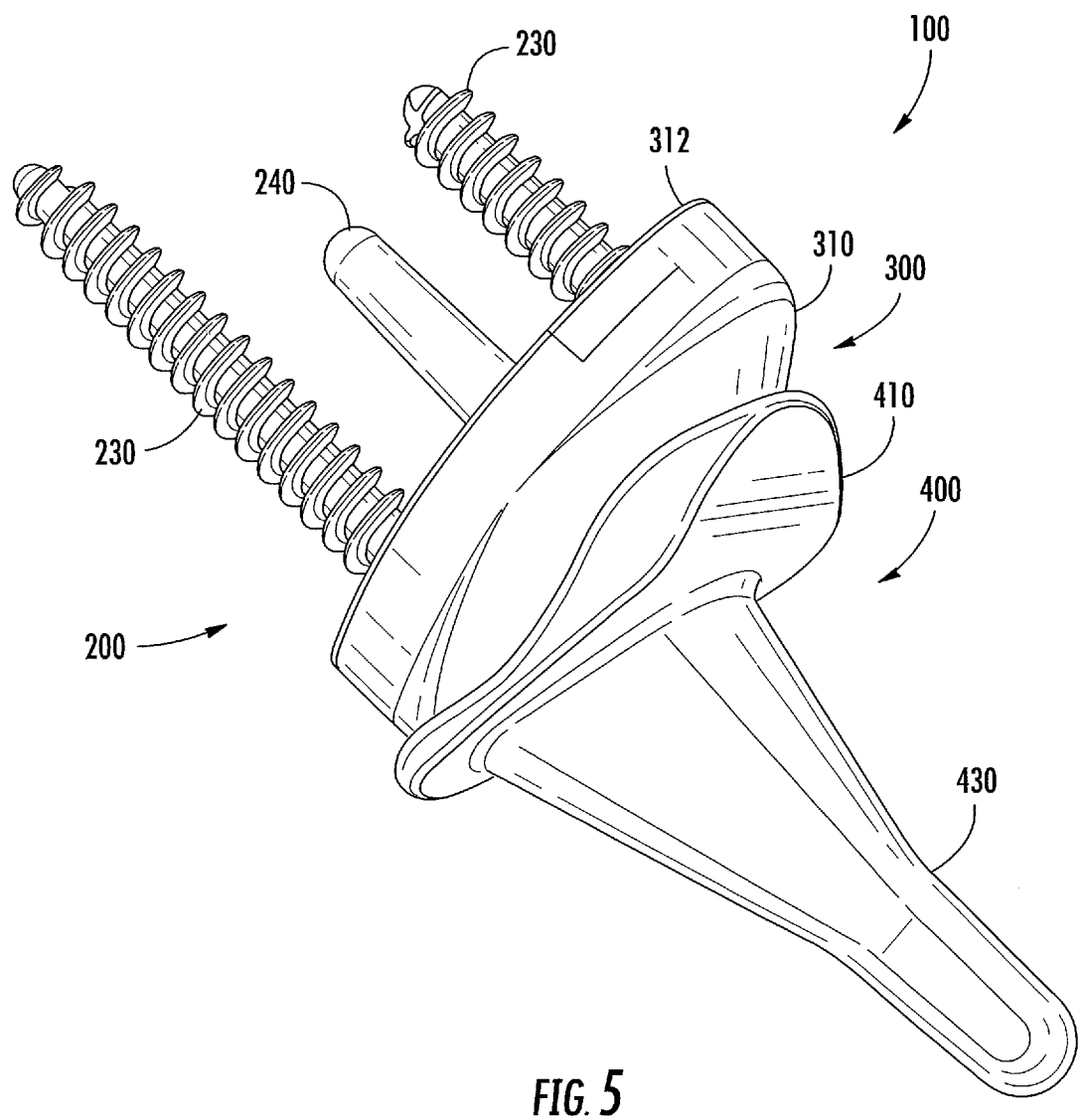

FIGS. 2 to 7 illustrate embodiments of a prosthetic wrist implant or implant system 100. System 100 can comprise a radial implant component 400, a carpal implant component 200, and an articulating bearing component or bearing member 300 provided or placed therebetween. Carpal implant component 200 can comprise a substantially planar carpal plate 210 having a distal surface 212 and an opposing proximal surface 214 with at least one socket protrusion 216 extending therefrom. Carpal implant component 200 can further include an elongated carpal post member or post 240 adapted for fixation to one or more carpal bones of carpal complex 32 (FIG. 1) and one or more apertures 218 for receiving one or more screws 230 (FIG. 5). Radial implant component 400 can comprise a radial tray 410 having a distal bearing surface 412 and an opposing proximal surface 414. An elongated radial stem 430 can extend from proximal surface 414 and can be adapted for fixation to a radius bone 12 (FIG. 1). Elongated radial stem 430 can be off-center from and/or comprise a non-centered position in relation to a center of proximal surface 414. Bearing member 300 can articulate or move over portions of distal bearing surface 412 of radial implant component 400.

Figure 17:
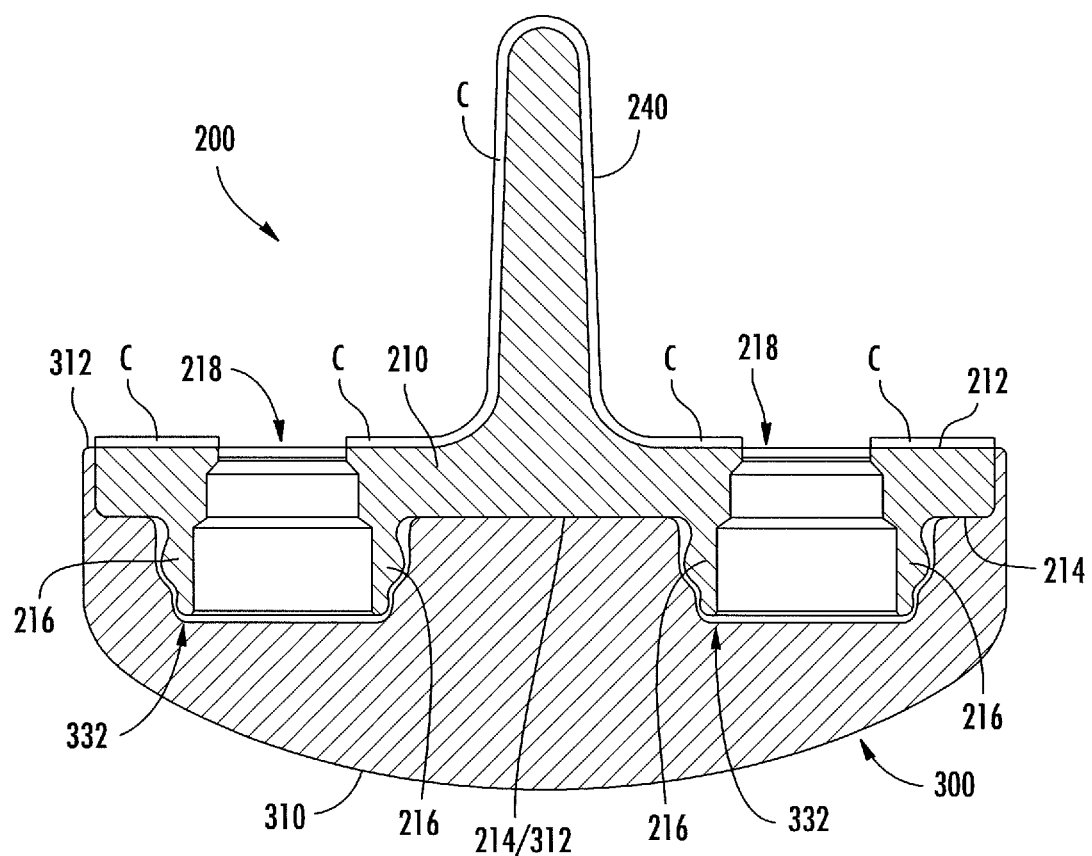
FIG. 17 is a cross sectional view illustrating a carpal insert component coupled to a bearing component or bearing member.

Articulating bearing member 300 can be disposed between portions of carpal implant component 200 and radial implant component 400 and/or can be adapted to physically communicate or engage portions of each component. Bearing member 300 can comprise a proximal bearing surface 310 and a distal surface 312 defining at least one socket recess 332 (FIG. 17). Proximal bearing surface 310 can be configured to articulate with respect to and/or move over portions of distal bearing surface 412 for simulating complex motions associated with wrist movement. Socket recess 332 (FIG. 17) can be adapted to cooperate with and/or receive portions of each socket protrusion 216 of carpal implant component 200. Proximal bearing surface 310 can be adapted for cooperative engagement with distal bearing surface 412 of radial implant component 400. In one aspect, one or more socket protrusion 216 of carpal implant component 200 can be adapted to linearly engage one or more socket recesses 332 (FIG. 17) of bearing member 300 to desirably limit rotational and translational movement of carpal implant component 200 relative to bearing member 300.

Figure 6:
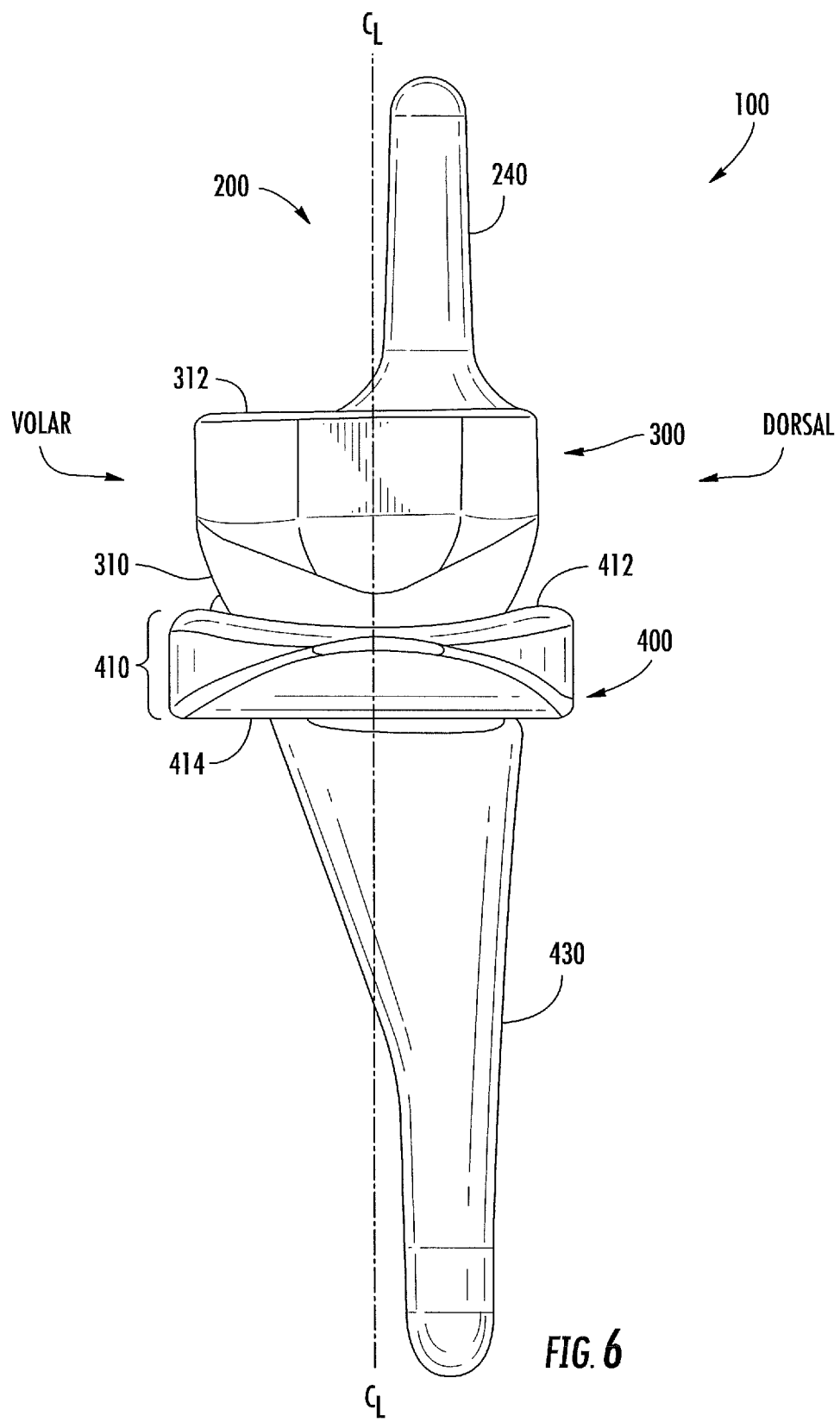
Figure 7:
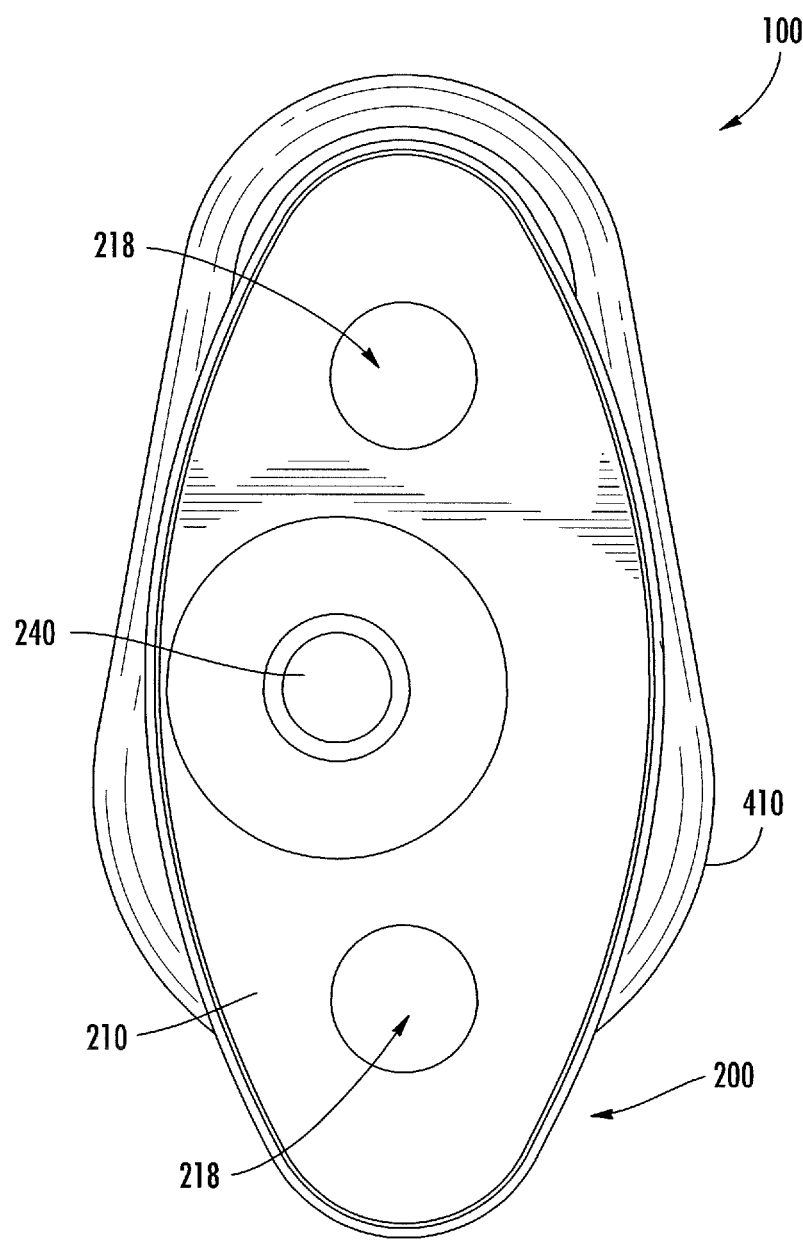

Still referring to FIGS. 2 to 7, carpal implant component 200 can comprise a carpal plate 210 and one or more screws 230 (FIG. 5). Screws 230 can be adapted to cooperate with portions of one or more carpal bones of complex 32 (FIG. 1). Carpal plate 210 can comprise a post 240 extending distally for implantation into a portion of capitate bone 24 (FIG. 1). Post 240 can be substantially cylindrical and/or tapered in shape and can be substantially vertical with respect to carpal plate 210. In one aspect, outer surfaces of post 240 can be tapered, such that post is wider at a bottom portion than at a top portion. FIG. 6 illustrate post 240 and stem 430 offset or off-center along a same side (e.g., towards the dorsal side) with respect to a center of bearing 300 and/or radial plate 410. FIG. 6 also illustrates volar and dorsal sides of system 100, as implanted. FIG. 7 illustrates, post 240 can be non-centered with respect to plate 210. Post 240 can extend substantially parallel to but in an opposite direction from radial stem 430.

Referring to FIG. 5, one or more screws 230 can be cannulated or non-cannulated and can be inserted through one or more apertures 218 (FIGS. 2, 7) of plate 210 and into one or more carpal bones 32 (FIG. 1) at variable angles. Screws 230 can optionally comprise locking caps 1080 (FIG. 44) that can be screwed into portions of plate 210. Radial implant component 400 can comprise a monoblock construction or device configured to be implanted into portions of radius 12. Radial implant component 400 can comprise a tray 410 having a substantially concave distal bearing surface 412 which can articulate with a similarly shaped convex proximal bearing surface 310 of bearing member 300. Extending proximally from tray 410 is a radial stem 430, which can be completely embedded into portions of radius 12 (FIG. 1).

Figure 8A:
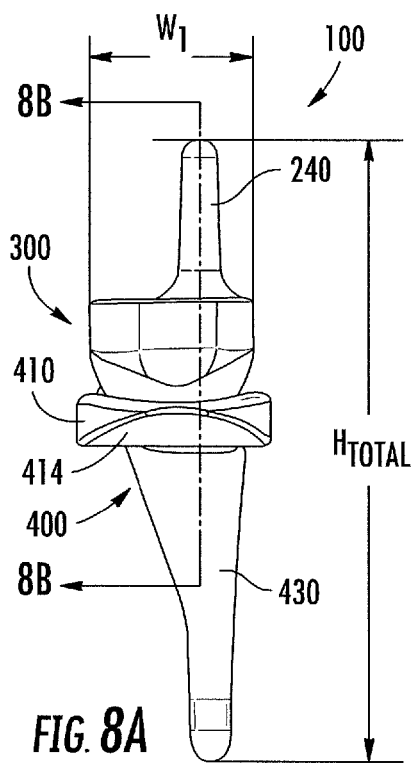
FIGS. 8A and 8B are, respectively, perspective and cross sectional views illustrating a wrist implant.
Figure 8B:
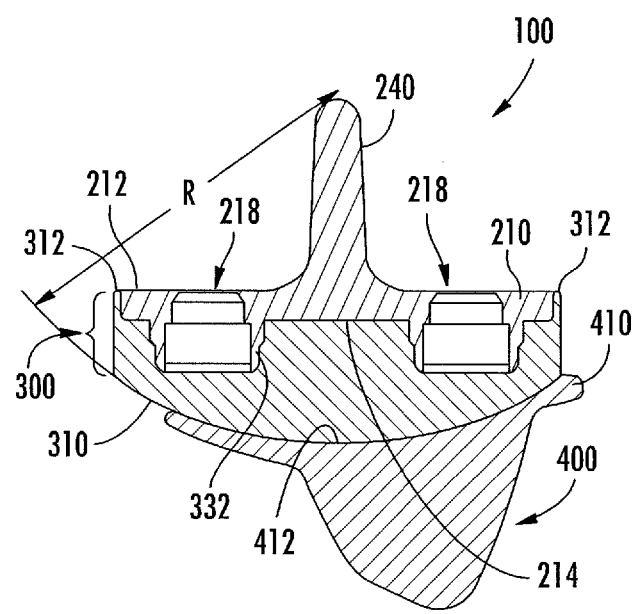
Figure 9A:
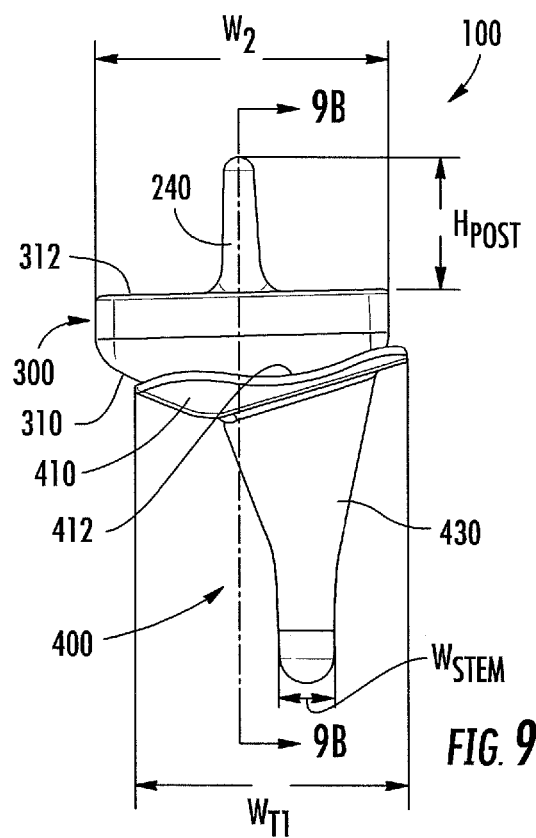
FIGS. 9A and 9B are, respectively, perspective view and cross sectional views illustrating a wrist implant.
Figure 9B:
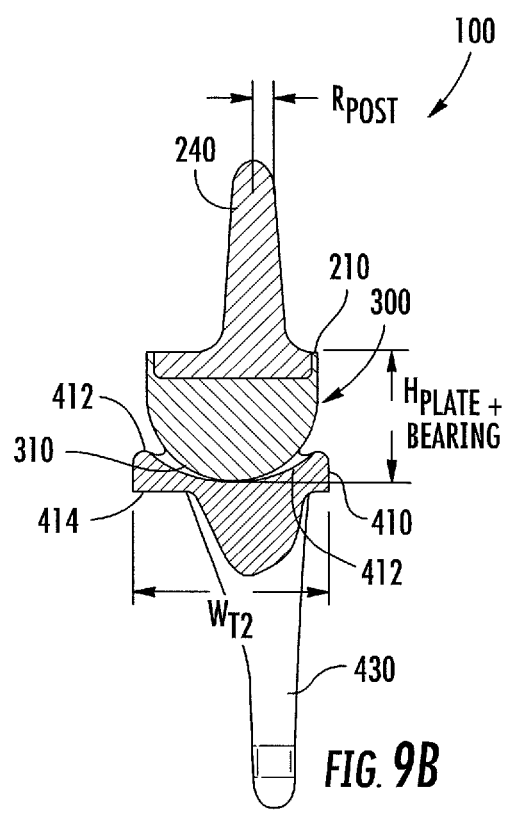

Wrist implant systems 100 can be offered in multiple sizes, for example four sizes, with Size 1 being the smallest and Size 3 being the largest. Size 2 may be a commonly used size. FIGS. 8A and 8B and FIGS. 9A and 9B illustrate various generic measurements of wrist implant system 100. FIG. 8A is a perspective view of system 100 from an ulnar side of radial tray 410 and includes generic measurements of a first width $W_1$ of carpal plate 210 and a total height $H_{TOTAL}$ of implant system 100. FIG. 8B is a cross sectional view along lines 8B-8B, which is a cross-section taken from a plane perpendicular to the plane of a radial/ulnar deviation radius of curvature (e.g., first radius of articulation 446, FIG. 11B) of radial tray 410 and shows radius R of the curve. Radius R can coincide with a top of carpal post 240 to an articulating surface 310 of bearing member 300, but does not have to. FIG. 9A is a perspective view of system 100 from dorsal side of radial tray 410 and shows a second width $W_2$ of carpal plate 210, height $H_{POST}$ of carpal post 240, a width $W_{STEM}$ of radial stem 430, and a width $W_{T1}$ of radial tray 410. FIG. 9B is a cross section along lines 9B-9B in FIG. 9A and illustrates generic measurements of a tip radius $R_{POST}$ (e.g., of a tip of post 240), a variable second width $W_{T2}$ of radial tray 410, and a height $H_{PLATE+BEARING}$ from distal surface 212 of carpal plate 210 to a lowermost point of articulating surface 310 of bearing member 300.

Referring to FIGS. 8A-9B, in one aspect, sizes of wrist implant (e.g., sizes 1-3) can comprise basic dimensions such as, for example and without limitation: $W_1$ between approximately 14 mm and 18 mm; $W_2$ between approximately 29 mm and 37 mm; $H_{TOTAL}$ between approximately 51 mm and 70 mm; R between approximately 25 mm and 32 mm; $H_{POST}$ between approximately 14 mm and 17 mm; $W_{STEM}$ between approximately 5 mm and 7 mm; $W_{T1}$ between approximately 28 mm and 35 mm; $R_{POST}$ between approximately 1 mm and 2 mm, such as approximately 1.75 mm; $W_{T2}$ between approximately 16 mm and 21 mm; and $H_{PLATE+BEARING}$ between approximately 10 mm and 15 mm. However, implants, components, and systems are not a "one size fits all" construction, thus, multiple sizes, dimensions, and any suitable measurements of components are contemplated herein, and are not limited to the sizes shown and described above.

Figure 10:
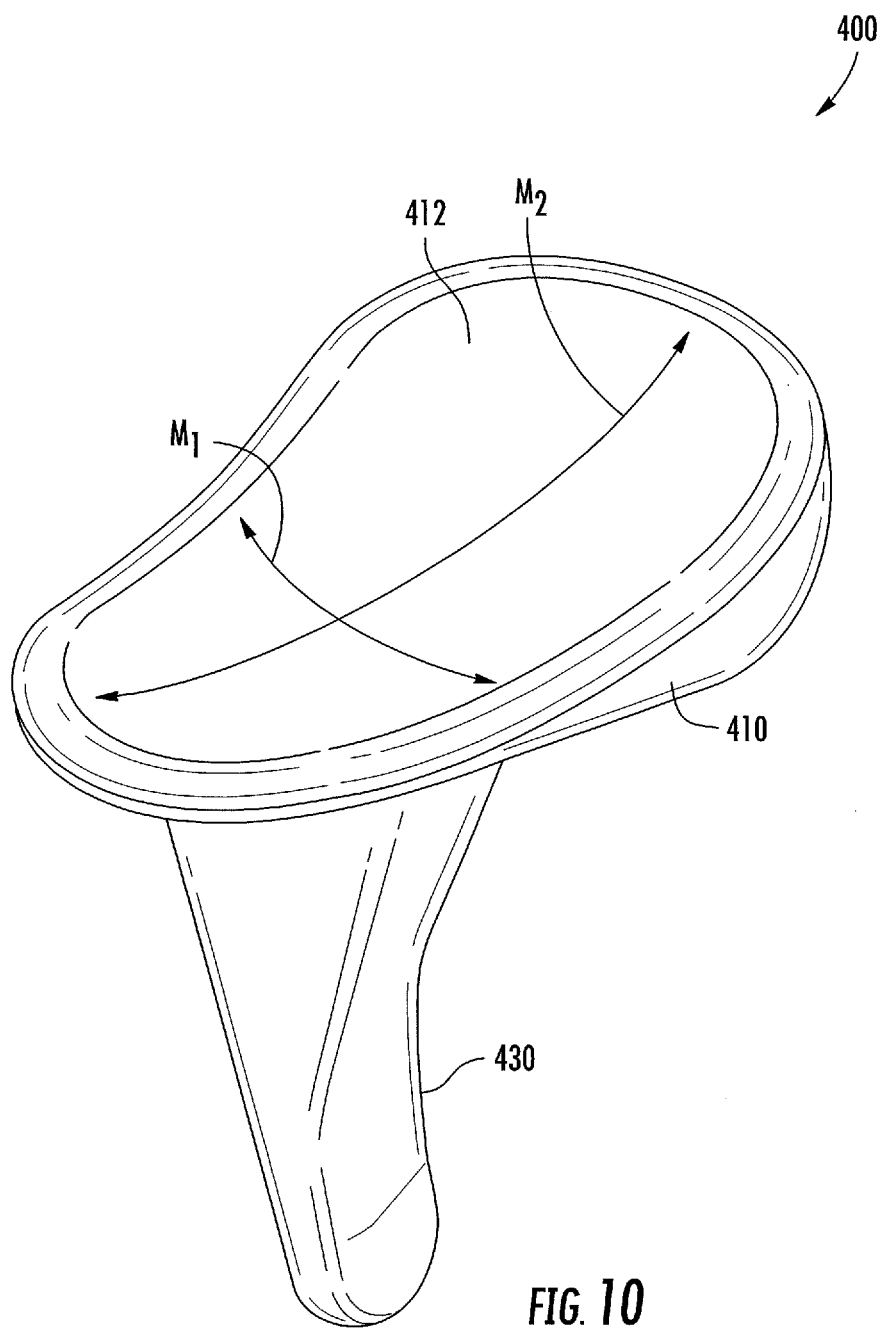
FIG. 10 is a perspective view illustrating a radial implant component.

Referring now to FIGS. 10 and 11, generally, implant articulation surfaces such as articulation surfaces of bearing member 300 and/or radial implant component 400 can be either ellipsoid or toroid in shape. Notably, in each case, there can be at least two different radii of articulation, which may be constant and/or vary for allowing movement of bearing member 300 with respect to radial implant component 400 in at least two general directions, generally designated $M_1$ and $M_2$ in FIG. 10. Movement in directions $M_1$ and $M_2$ can mimic natural movement within a wrist, thus, advantageously providing a system for relieving wrist pain without causing loss of wrist movement. Implant components, systems, and methods described herein can advantageously improve prosthetic wrist implants, in one aspect, by providing a greater degree of freedom in the joint via multi-directional movement.

As FIGS. 10 to 11E illustrate, movement of bearing 300 along a distal bearing surface of tray 410 can include movement along bearing surface 412 in a first direction $M_1$ and a second direction $M_2$. Bearing surface 412 of tray 410 can comprise a first radius of articulation generally designated 446 (FIG. 11B) and a variable second radius of articulation generally designated 442 (FIGS. 11C to 11E). First radius of articulation 446 can comprise a radial/ulnar deviation radius of curvature allowing for motion that exists in a coronal plane, such as motion along direction or line $M_1$ (FIG. 10). Variable second radius of articulation 442 (FIGS. 11C to 11E) can comprise a flexion/extension radius of curvature allowing for motion or movement along a second direction $M_2$ (FIG. 10) that exists in the sagittal plane. Second radius of articulation 442 of radial implant component 400 can comprise a flexion/extension radius of curvature that varies along the radial/ulnar direction. Both of these radii may be constant through an entire range of motion and first radius of articulation 446 (e.g., radial/ulnar deviation radius of curvature) can be larger than second radius of articulation 442 (e.g., flexion/extension radius of curvature). Flexion/extension radius of curvature or second radius of articulation 442 of implant system 100 can vary along the constant radial/ulnar deviation radius of curvature (e.g., 446). This means that as the wrist goes into radial deviation, it has a larger arc of flexion/extension motion. The terms "radius of curvature," "radius of articulation," and "articular radius" are used interchangeably herein.

As further illustrated by FIGS. 10 to 11E, radial implant component 400 can have at least one variable radius and/or radii of articulation (e.g., 442 and 446) optionally in combination with a variable width $W_X$ of radial tray 410. The variable width $W_X$ of radial tray 410 refers to an outer profile of tray 410 when viewed axially (from distal to proximal). As FIGS. 11A to 11E illustrate, the tray 410 can get wider from a radial side 418 to an ulnar side 420. Having a variable radius of articulation describes the manner in which articular bearing surface 412 of radial implant component 400 can be designed. For example, a flexion/extension radius of curvature (e.g., 442) can vary, generally or continuously, from radial side 418 to ulnar side 420 of radial tray 410. In one embodiment, for example, and as illustrated in FIGS. 11A to 11E, a flexion/extension radius of curvature (e.g., 442) proximate ulnar side 420 can be larger than the flexion/extension radius of curvature proximate radial side 418 of radial tray 410, resulting in a teardrop shaped tray 410.

In one embodiment, radial tray 410 can be wider on ulnar side 420 than on a radial side 418. FIGS. 11B to 11D illustrate different cross sections of radial implant component 400 in 11A. FIG. 11B is taken from approximately the center of tray 410 and shows a radial/ulnar deviation radius of curvature, or first radius of articulation 446 in the coronal plane. FIGS. 11C to 11E are taken from three different plane locations of tray 410 that are perpendicular to the plane having the radial/ulnar deviation radius of curvature shown in FIG. 11B. FIG. 11C is at a distance closest to radial side 418 of tray 410 and can be approximately 25% of the distance between radial side 418 and ulnar side 420. Similarly, FIG. 11D can be approximately 50% and FIG. 11E can be approximately 75% of the distance between radial and ulnar sides 418 and 420, with FIG. 11E being closest to ulnar side 420. The diagonal lines are in the planes of the section cuts in each of the section views. As shown in the section views, both flexion/extension radius or second radius articulation radius 442 and variable width $W_X$ of tray 410 increase going from radial side 418 to ulnar side 420 of tray 410.

Additionally, as seen in FIGS. 11C to 11E, flexion/extension radius of curvature, e.g., second radius of articulation 442 increases, generally or continuously, from radial side 418 to ulnar side 420 of radial tray 410. More specifically, a radius of curvature at a first location R1 can be smaller than a radius of curvature at a second location R2, which can be smaller than a radius of curvature at a third location R3. Second radius of articulation 442 (e.g., flexion/extension radius of curvature) can comprise any different or suitable value depending upon the size of implant components within system 100. For example, first radius of curvature R1 closest to radial side 418 can range from about 8 mm to about 14 mm; second radius of curvature R2 can range from about 9 mm to 15 mm; and third radius of curvature R3 closest to ulnar side 420 can range from about 10 mm to 16 mm. Additionally, radial tray 410 can be wider on ulnar side 420 than on radial side 418. More specifically, variable width $W_X$ can comprise a first width $W_{1X}$ that can be smaller than a second width $W_{2X}$ that can be smaller than a third width $W_{3X}$ along a length of plate 410. Variable width $W_X$ can vary depending on the size of implant components within system 100. First width $W_{1X}$ can range from about 10 mm to about 18 mm; second width $W_{2X}$ can range from about 13 mm to 21 mm; and third width $W_{3X}$ can range from about 16 mm to 24 mm. As FIG. 11B illustrates, the radial/ulnar deviation radius of curvature or first radius of articulation 446 can be constant. However, it will be appreciated that the radial/ulnar deviation radius of curvature (e.g., first radius of articulation 446) can vary along the dorsal/volar direction, if desired.

Figure 12:
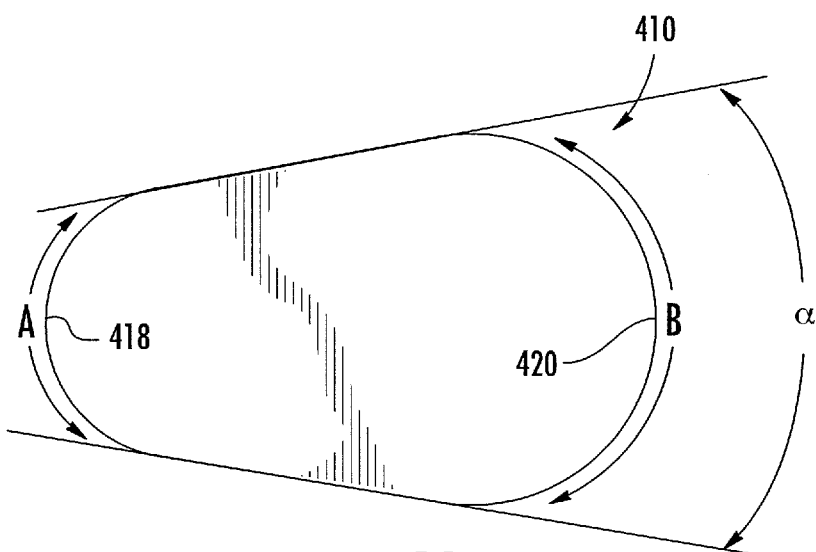
FIG. 12 is a schematic diagram of an outer profile of the radial tray.
Figure 13:
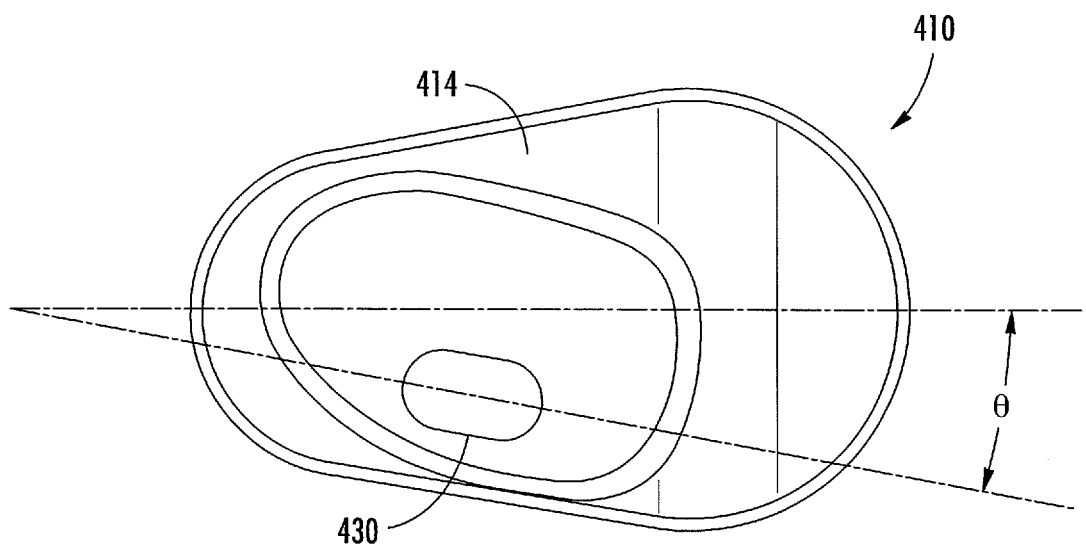
FIG. 13 is a diagram illustrating rotation of the radial stem on a proximal surface of the radial tray.

As FIGS. 12 and 13 illustrate, a profile of tray 410 can comprise a shape made up of two arcs, a first arc A on radial side 418 and a second arc B on ulnar side 420. Tray 410 can comprise an angle α disposed between two lines which connect and/or are tangent opposing sides or portions of arcs A and B, where the radius of arc B can be larger than the radius of arc A. The two lines can intersect and have angle α therebetween which can be greater than zero. Tray 410 can increase in width, generally or continuously, from radial side 418 to ulnar side 420 up to a certain point at which it can decrease and can culminate in arc B.

A variable articulation radius of wrist implant system 100 in accordance with the present subject matter can advantageously decrease congruity between the carpal and radial articulation surfaces and therefore allow for a greater degree of freedom in the joint. The incongruity of articulating surfaces can also advantageously increase the stability of the implant. Additionally, at least one variable radius of articulation (e.g., 442), particularly when combined with variable tray width $W_X$, can allow for a greater degree of freedom, as it allows for rotation and translation of carpal implant component 200 on or over radial implant component 400. Notably, this rotational and translation movement can allow implant system 100 to more closely mimic or approximate natural wrist movement.

Furthermore, at least one variable radius of articulation as described in the present subject matter can allow even more rotation of carpal implant component 200 with respect to radial implant component 400 along with some translation, which decreases an amount of stress transferred to the implant/bone interface and therefore can improve long-term fixation. Thus, where there is a variable radius of articulation there is less congruency in total wrist system 100 (FIG. 2) and less congruency in total wrist system 100 results in less dislocation, making implant system 100 more stable. Since dislocation of wrist implants commonly occurs in flexion mixed with supination of the wrist, the design of variable radii of articulation (e.g., second radius of articulation 442) can reduce dislocation because articulation allows for greater travel of carpal implant component 200 in that type of motion. Notably, the profile shape of radial tray 410 that results from a variable tray width design can closely resemble the shape of the natural radius 12.

In one embodiment, radial implant component 400 can be made of cast material comprising, for example, CoCrMo specified per ASTM F75. However, it will be appreciated by those skilled in the art that other materials having sufficient strength and biocompatibility can also be employed. Other total wrist implants tend to force the wrist into an unnaturally pronated position. However, the rotation of radial tray 410 with respect to radial stem 430 and/or variable radius of articulation can allow the wrist implant components and/or system to be in a more natural anatomical position of slight supination.

In one aspect, radial tray 410 can be rotated. This refers to tray 410 of radial implant 400 being in a position with respect to stem 430 that is rotated from neutral. For example, the plane in which the radial/ulnar deviation radius of curvature arc (e.g., first radius of articulation 446) is defined can be rotated with respect to the stem 430 center plane. FIG. 13 shows rotation of stem 430 with respect to a plane of the teardrop-shaped tray 410 of the preferred embodiment. The rotation of a portion of stem 430 can be in the range of an angle θ that is more than 0 degrees (°) but less than 90°, either clockwise or counterclockwise, such as approximately 3° to 20°, 5° to 15°, or about 5°, clockwise for a left wrist with respect to tray 410 when viewed from proximal to distal or counterclockwise for a right wrist when viewed from proximal to distal.

Figure 14:
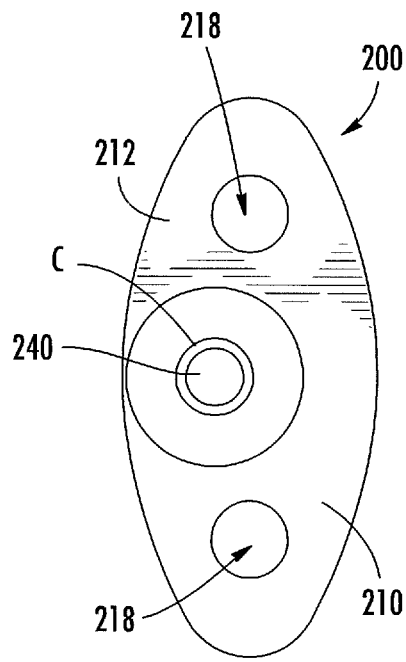
FIGS. 14-16 are various perspective views illustrating a carpal implant component.
Figure 15:
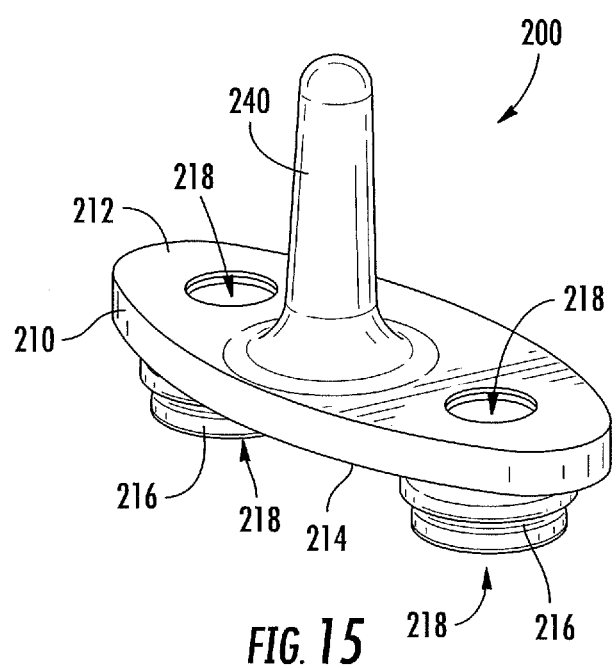
Figure 16:
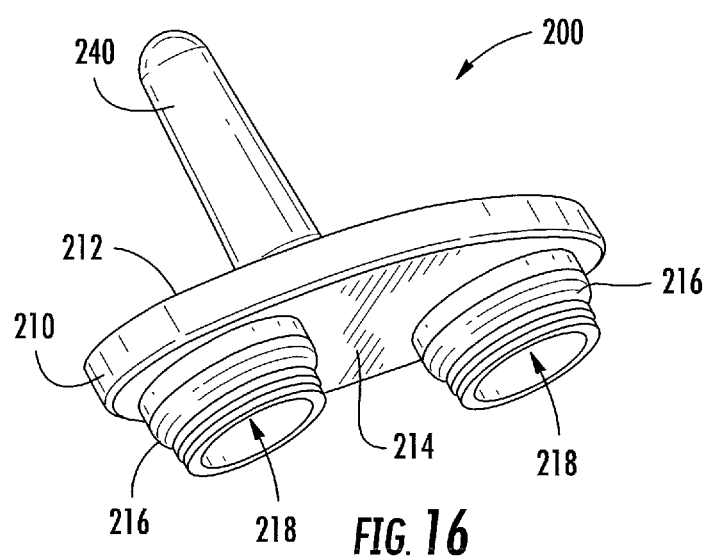

FIGS. 14 to 16 illustrate various views illustrating carpal implant component 200. FIG. 14 is a top perspective view illustrating distal surface 212 of carpal plate 210 configured to attach to one or more carpal bones of complex 32 through elongated carpal post 240. Carpal implant component 200 can comprise titanium, such as Ti-6Al-4V ELI as per specification ASTM 136, although it will be appreciated by those skilled in the art that other materials having sufficient strength and biocompatibility can also be employed. In order to accommodate the different wrist sizes found in a variety of patients, carpal implant component 200 can be made in multiple sizes, such as four sizes, with sizes ranging from Size 1 to Size 3, Size 1 being the smallest and Size 3 being the largest.

Elongated carpal post member or post 240 can protrude substantially perpendicularly from distal surface 212 of carpal implant component 200, as illustrated in FIG. 15. The entire length of post 240 can taper towards plate 210 such that post 240 is wider at a portion directly adjacent plate 210. One or more apertures 218 can extend through plate 210 as shown, such that one or more anchoring members or screws (e.g., 230, FIG. 5) can be positioned and secured therein. Post 240 and/or distal side of plate 210 can comprise a metal coating C (FIGS. 14 and 17), such as a titanium coating, for example porous beaded or plasma-sprayed coating of Commercially Pure (C.P.) Titanium powder as per ASTM F1580 requirements, which serves to secure post 240 into carpal bone complex 32 once it is implanted by enhancing the press-fit relationship between post 240 and carpal bone complex 32 and by aiding in osteointegration of implant system 100. However, it will be appreciated by those skilled in the art that other materials having sufficient strength and biocompatibility can also be employed. As described in more detail below, carpal post 240 can be inserted into a portion of capitate bone 24 and can include bone screws 230 (FIG. 5) configured for insertion into apertures 218 and extension through the carpal plate 210. Screws 230 can then be secured e.g., via screwing into hamate 22 and trapezoid bones 26.

Still referring to FIGS. 14-16, carpal plate 210 can comprise proximal surface 214 and opposing distal surface 212. Distal and proximal surfaces 212 and 214 can be substantially planar, or non-planar. Proximal surface 214 can be configured to couple to a portion of distal surface 312 of bearing member 300 by a coupling mechanism and/or frictional engagement. Socket protrusions 216 can be configured to engage, fit, couple, and/or communicate with recessed portions or socket recesses 332 (FIG. 17) of bearing member 300. Bearing member 300 can be configured to imitate the articulation of wrist bones and can be adapted for placement between portions of radial implant component 400 and carpal implant component 200.

Referring to FIG. 17, bearing member 300 can include an at least substantially planar distal surface 312 and an opposing and substantially convex articulating proximal bearing surface 310 which can articulate against the corresponding radial tray 410 of the radial implant component 400. Bearing member 300 can comprise a plastic material such as polyethylene, such as ultra-high molecular weight polyethylene (UHMWPE). However, it will be appreciated that other low friction polymeric materials can also be employed. In addition, other materials can also be used in some situations. In order to accommodate the different wrist sizes found in a variety of patients, bearing member 300 can be made in four sizes ranging from Size 1 to Size 3, to correspond to carpal plate 210. Additionally, in order to accommodate the extent of radius bone 12 resection, bearing member 300 can have three variations of height: (i) standard, (ii) +2 mm taller, and (iii) +4 mm taller. It is appreciated that bearing member 300 can be configured as an integral part of carpal implant component 200 and/or comprise the same material as carpal plate 210.

Bearing member 300 can comprise recessed portions or socket recesses generally designated 332 disposed adjacent portions of proximal surface 214 of carpal plate 210. Recessed portions can be configured to receive and engage socket protrusions 216 disposed on proximal surface 214 of carpal implant component 200. Socket protrusions 216 can extend from proximal surface 214, and socket recesses 332 can be aligned with apertures 218. Additionally, it is contemplated that each recessed portion (e.g., 332) can comprise tapered inner walls and can comprise varying diameters along the length. Socket protrusions 216 can be shaped to integrally fit within recessed portions or socket recesses 332, such that a portion of distal surface 312 of bearing member 300 can be substantially planar with a portion of proximal surface 214 of carpal plate 210 when carpal implant component 200 and bearing member 300 are fittingly engaged and/or coupled together. Additionally, when carpal implant component 200 and bearing member 300 are coupled together, portions of socket protrusions 216 can be aligned with socket recesses 332 to create a unitary component. Post 240 and distal surface 212 can comprise a metallic coating C, such as a titanium coating, for example porous beaded or plasma-sprayed coating of C.P. titanium powder.

In addition to the aspects of the wrist implant system 100 described above, the wrist implant system 100 of the present subject matter can comprise other optional features. For example, regarding carpal implant component 200, carpal post 240 can be tapered to increase fixation of the carpal implant component 200 to one or more carpal bones 32, while a length of carpal post 240 can be decreased to prevent violating the third carpometacarpal joint. Additionally, an end radius of carpal plate 210 and a corresponding carpal poly profile can be larger in order to achieve smoother motion of implant system 100. Additionally, carpal screws 230 (FIG. 5) can have additional features such as a hydroxyapatite coating for enhanced fixation of carpal implant component 200 in carpal bone complex 32 and apertures 218 can be threaded so that locking screws can be inserted over bone screws 230 (FIG. 5) to lock into place. The carpal implant component 200 may have a flange that sits outside the capitate when the carpal plate is implanted.

Regarding radial implant component 400, radial stem 430 can be enlarged as needed to improve the fit between the distal radius, and a dorsal/radial corner of radial stem 430 can be less prominent in order to reduce the possibility of hitting the radial cortex in that area. Additionally, a length of radial stem 430 can be shortened in order to be less invasive within radius 12. Radial stem 430 can optionally be lengthened and/or comprise a larger diameter as a larger radial stem body allows an articular surface to be recessed proximally within the stem, resulting in less bone resection required and a smaller implant size. Alternatively, in one aspect the geometry of bearing member 300, carpal post 240, coupling mechanism, bone screws 230 for fixing carpal implant component 200 to one or more carpal bones 32, and/or instrumentation for implantation can be those described in U.S. Pat. Nos. 5,702,470, 6,059,832 and 7,531,003, each of which are incorporated herein by reference in their entireties.

Consequently, wrist implants or implant systems 100 and/or components thereof can be used in patients suffering pain and/or loss of function due to, for example, rheumatoid arthritis, scapholunate advanced collapse (SLAC), osteoarthritis or traumatic arthritis. Wrist implant system 100 and/or components can also be used in the revision of a failed implant or in situations where clinical experience indicates that other reconstructive efforts are not likely to achieve satisfactory results. In some patients with severe arthritis who do not qualify for total wrist arthroplasty, a hemiarthroplasty procedure can be used with only radial implant component 400 or only carpal implant component 200 in accordance with the present subject matter.

An example of a surgical technique or method for implanting prosthetic wrist implant or implant system 100 and/or components thereof is described below.

Pre-Operative Planning

A proper implant size can be estimated preoperatively via x-raying and/or x-ray templates. With carpal implant component 200 (FIG. 2) aligned with a center of the capitate 24 (FIG. 1), an ulnar screw should enter a proximal pole of hamate 22 (FIG. 1). In an anterior-posterior (AP) view, radial implant component 400 (FIG. 2) should not extend beyond the edge of the radial styloid. Carpal implant component 200 (FIG. 2) should not extend more than approximately 2 mm over margins of the carpus at the level of the osteotomy. In general, the smaller implant size should be selected when deciding between two sizes.

General Recommendations

Prophylactic antibiotic can be administered. Either general or regional anesthesia is also appropriate. A non-sterile tourniquet can be used. A strip of transparent adhesive film can be applied to a dorsum of the hand and wrist to protect the skin from damage during instrumentation. Fluoroscopy can be a helpful adjunct to confirm positions of the guides and implants. Resected bone can be saved for use in bone grafting the carpus to achieve an intercarpal arthrodesis.

Surgical Incision

Figure 18:
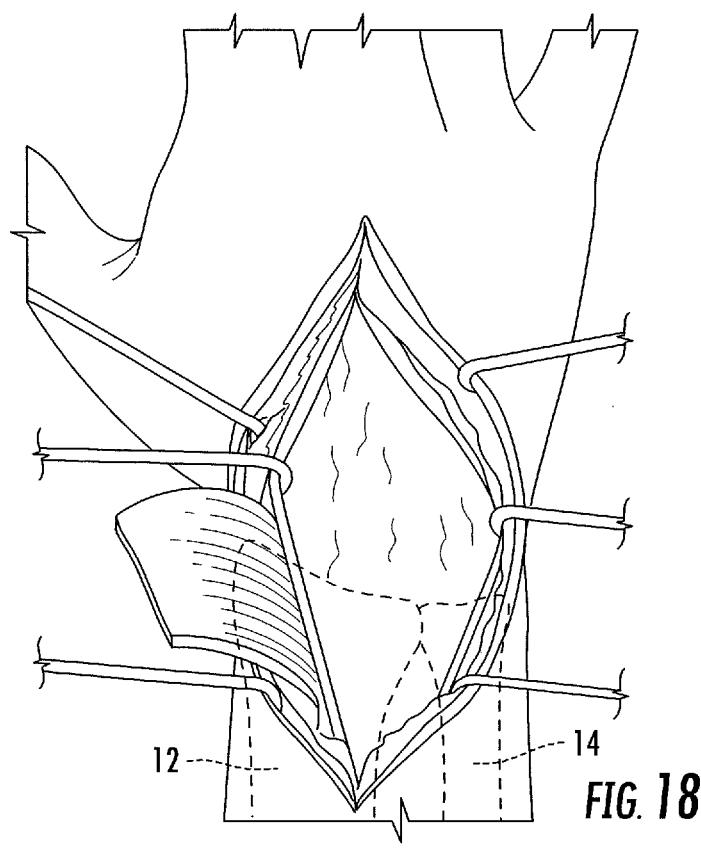

Referring to FIG. 18, a dorsal longitudinal incision can be made over the wrist in line with the third metacarpal, extending proximally from its midshaft. The skin and subcutaneous tissue can be elevated together off the extensor retinaculum, with care to protect the superficial radial nerve and the dorsal cutaneous branch of the ulnar nerve. The extensor carpi ulnaris (ECU) compartment can be opened along its volar margin and the entire retinaculum can be elevated radially to the septum between the first and second extensor compartments. Each septum can be divided carefully to avoid creating rents in the retinaculum, especially at Lister's tubercle, which may need to be osteotomized. An extensor tenosynovectomy is performed if needed, and the tendons are inspected. The extensor carpi radialis brevis (ECRB) must be intact or repairable (preferably the tensor carpi radialis longus (ECRL) is also functional). Vessel loops are used to retract the extensor tendon.

Joint Exposure

Figure 19:
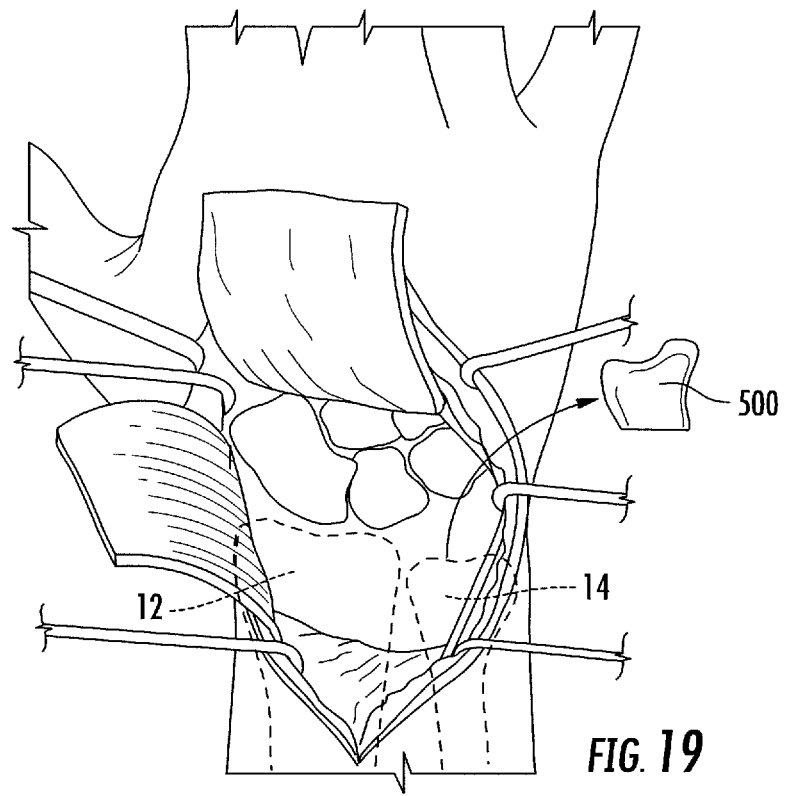

Still referring to FIG. 18, the dorsal wrist capsule can be raised as a distally based rectangular flap. As illustrated in FIG. 19, an ulnar head 500 can optionally be resected, and where resected, the capsule can be raised in continuity with the dorsal distal radioulnar joint (DRUJ) capsule and the periosteum over the distal 1 cm of the radius to create a broad exposure and long flap for closure. The sides of the flap can be made in the floors of first and 6th extensor compartments. If the distal ulna is to be preserved, the capsule on the ulnar side of the wrist is incised distal to the triangular fibocartilage complex (TFCC). The brachioradialis and first extensor compartment can be elevated subperiosteally from the distal styloid. The wrist can be fully flexed to expose the joint. Synovectomies of the radiocarpal and distal radioulnar joints can be performed, if needed. If the distal radioulnar joint is arthritic or if there is severe erosion of the distal radius, the distal ulna can be resected through its neck, or contoured into a cylinder. FIGS. 18 and 19 include portions of the radius 12 and ulna 14 illustrated in broken lines.

Preparation of Carpus

FIGS. 20 to 27 illustrate preparation of carpal bones of complex 32 (FIG. 1). A carpal size guide (not shown) can be placed on the dorsal surface of the carpus. The implant size most appropriate for the patient can be determined from the guide, which can show a centerline of post 240 of carpal implant component 200, as well as carpal screw insertion points. The line corresponding to ulnar screw should enter the pole of the hamate 22 (FIG. 1).

If scaphoid 16 and triquetrum 20 (FIG. 1) are mobile, carpus preparation can be facilitated by first temporarily pinning these bones to capitate 24 and hamate 22 in positions that create the most joint contact. K-wires can be left in place through final implantation of carpal implant component 200.

Lunate 18 (FIG. 1) or portions thereof can be excised by sharp dissection or rongeur. Referring to FIG. 20, a modular K-wire or drill guide, generally designated 600, comprises a barrel portion 602 pressed against capitate head and a saddle portion 604 placed onto the third metacarpal shaft over the skin. A sleeve 601 for a guide wire can be inserted in drill guide barrel portion 602. A 1.4 mm (0.054") guide wire can be drilled through capitate and into the third metacarpal. The sleeve 601 and drill guide 600 can be removed sequentially. As FIG. 21A illustrates, a 3.5 mm cannulated drill bit 606 can be placed over a guide wire 610 and as FIG. 21B illustrates, a hole H can be made in capitate. The hole can constitute a proper depth marked on drill bit 606.

Figure 22:
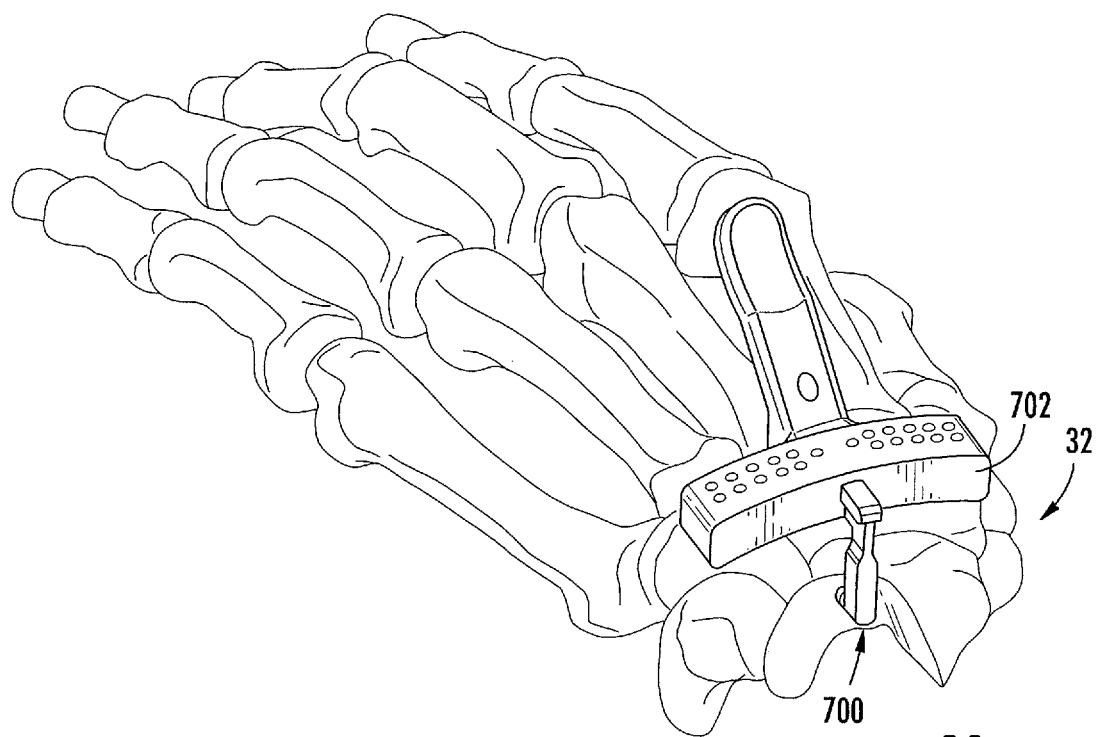
Figure 23:
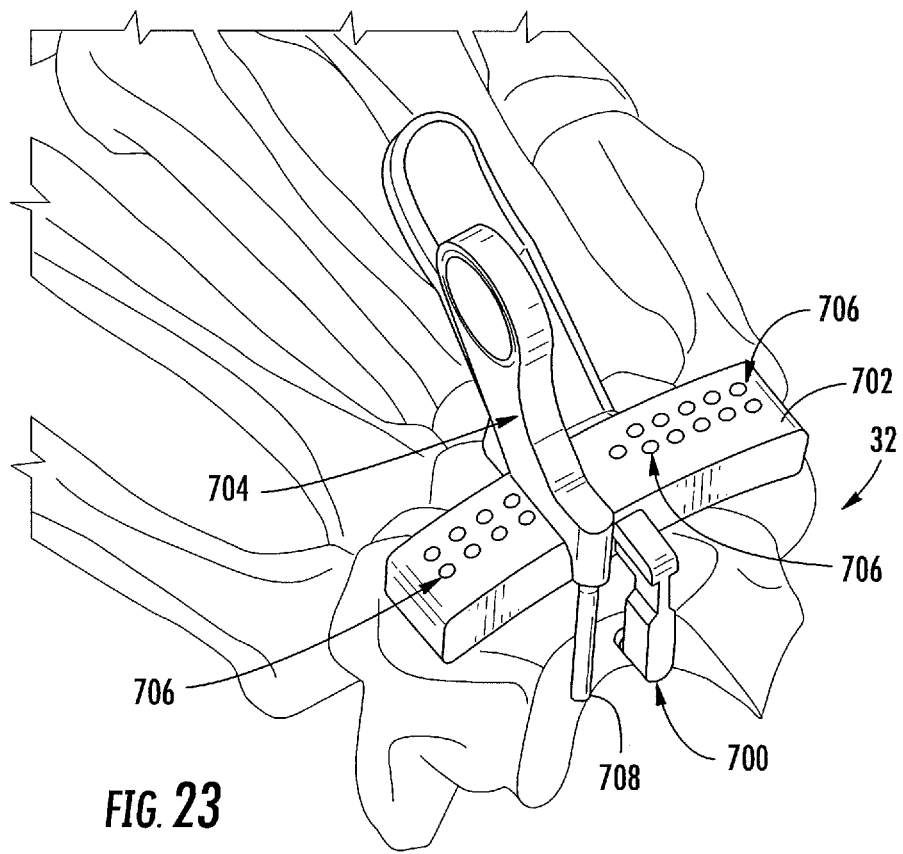

FIG. 22 illustrates a carpal guide bar generally designated 700 which can be inserted into a portion of hole H formed in capitate according to FIG. 21B, to its full depth. A carpal resection guide 702 can be mounted onto guide bar 700. FIG. 23 shows one or more posts of a hamate feeler, generally designated 704 inserted into a column of holes 706 on carpal resection guide 702, where holes 706 position a portion of hamate feeler 704 in a same sagittal plane as a pole of hamate. Carpal resection guide 702 can then be positioned such that a tip 708 of hamate feeler 704 just contacts a surface of hamate bone. A saw cut can pass through each of the proximal 1 mm of the hamate, the capitate head, the scaphoid waist, and the mid triquetrum.

Figure 24:
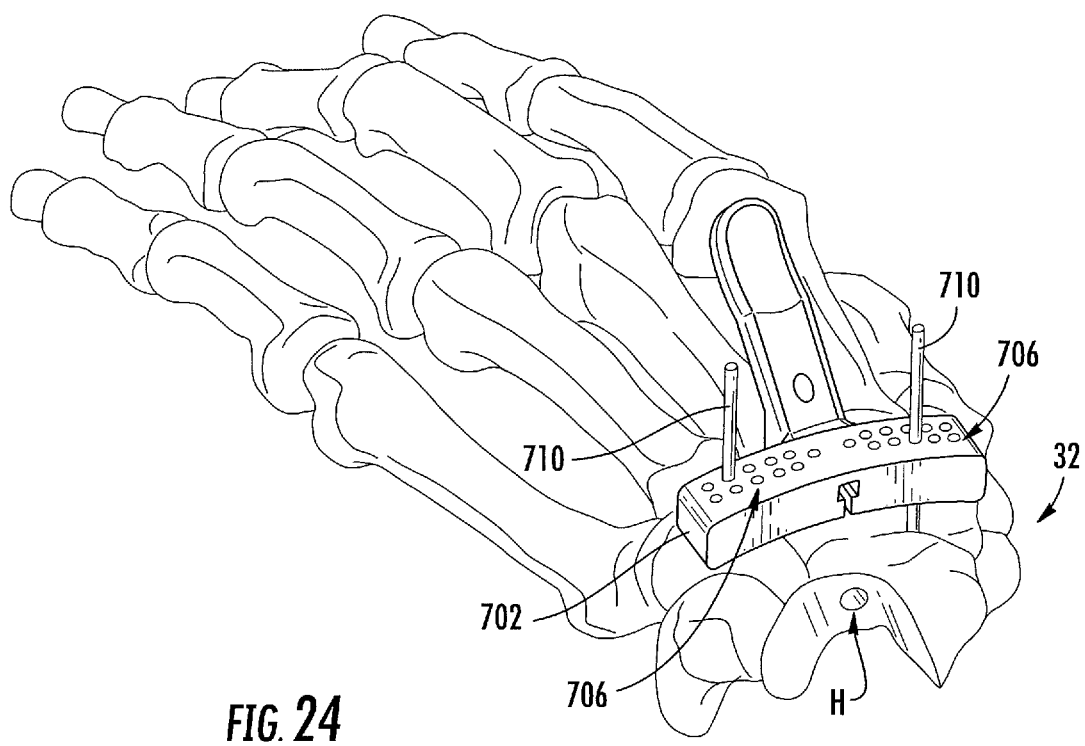

As FIG. 24 illustrates, while resection guide 702 is held aligned as described above, two to four 1.4 mm K-wires 710 can be inserted through holes 706 of resection guide 702 and drilled into the carpus. Resection guide 702 can comprise two rows of five holes on each half of resection guide 702, as well as a single hole placed between two rows on the medial end of each half. By using distal holes 706 in the rows, resection guide 702 can be adjusted distally to resect more carpus, if necessary. Carpal guide bar 700 can be removed and resection guide 702 can be pushed down onto carpus. K-wires 710 can be cut above resection guide 702. The position of resection guide 702 can be checked for proper level of resection. A cut can be made nearly perpendicular to the third metacarpal shaft.

Figure 2:
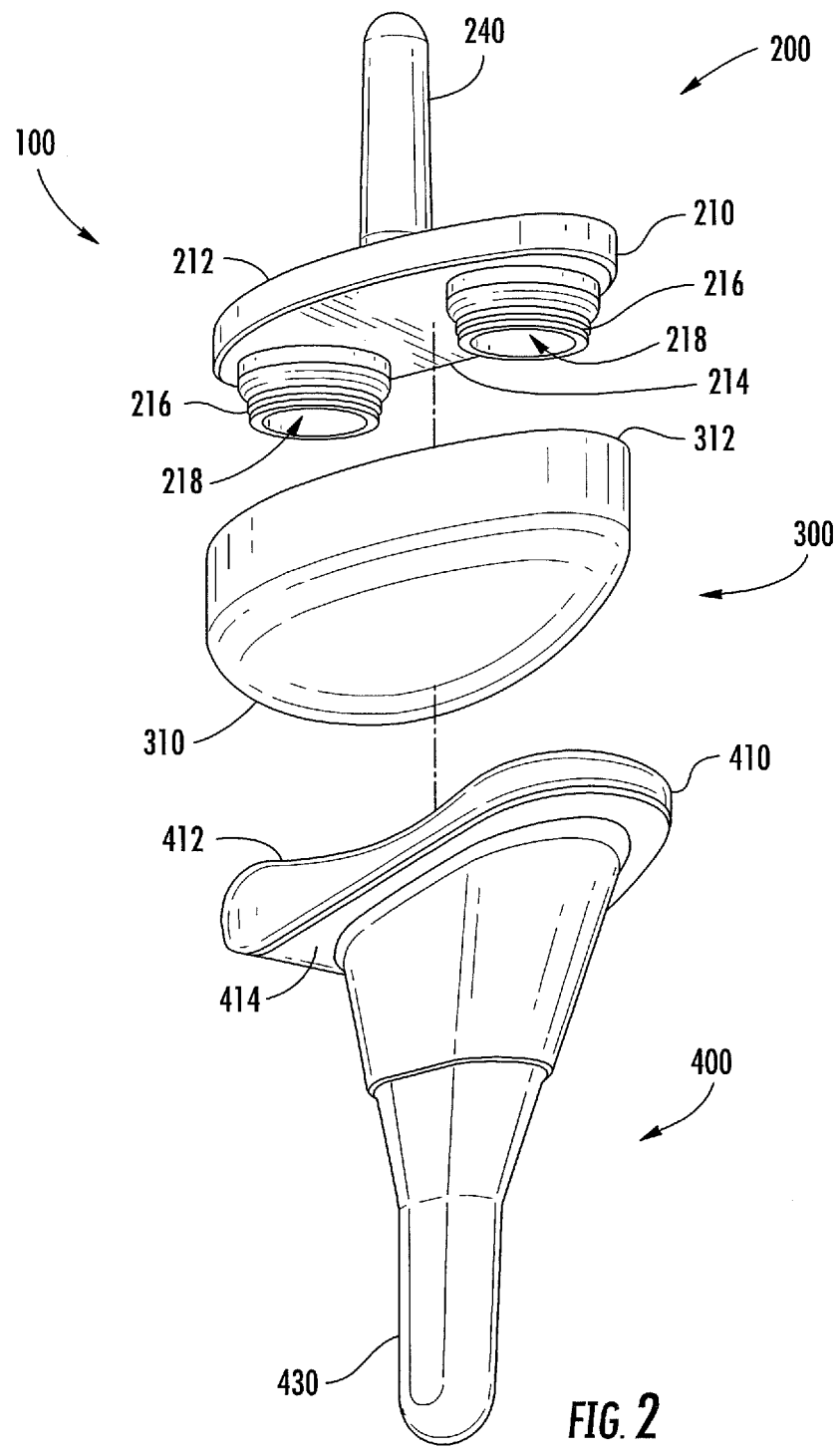
FIGS. 2-7 are various perspective views of a prosthetic wrist implant comprising wrist implant components.
Figure 3:
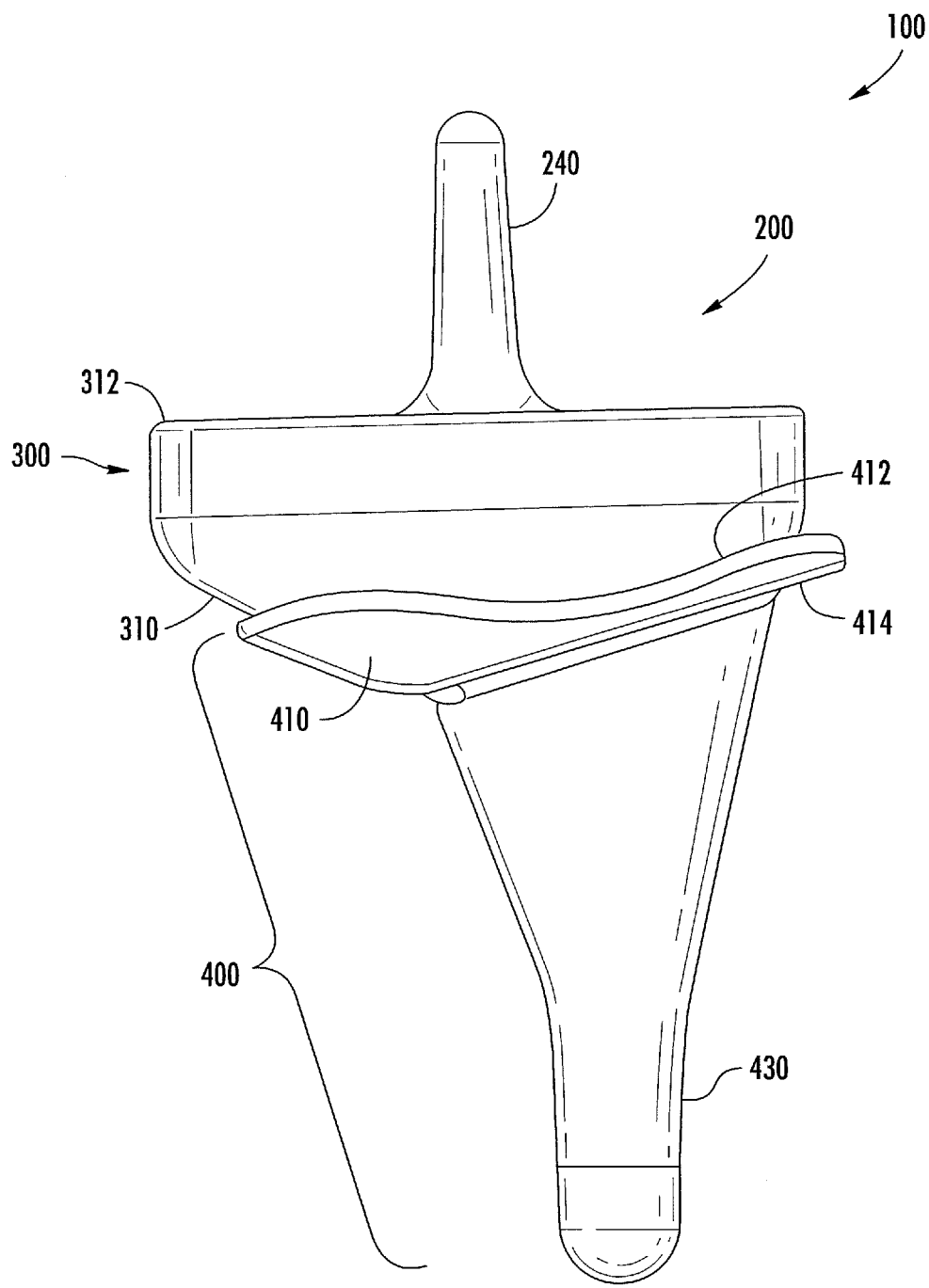
Figure 4:
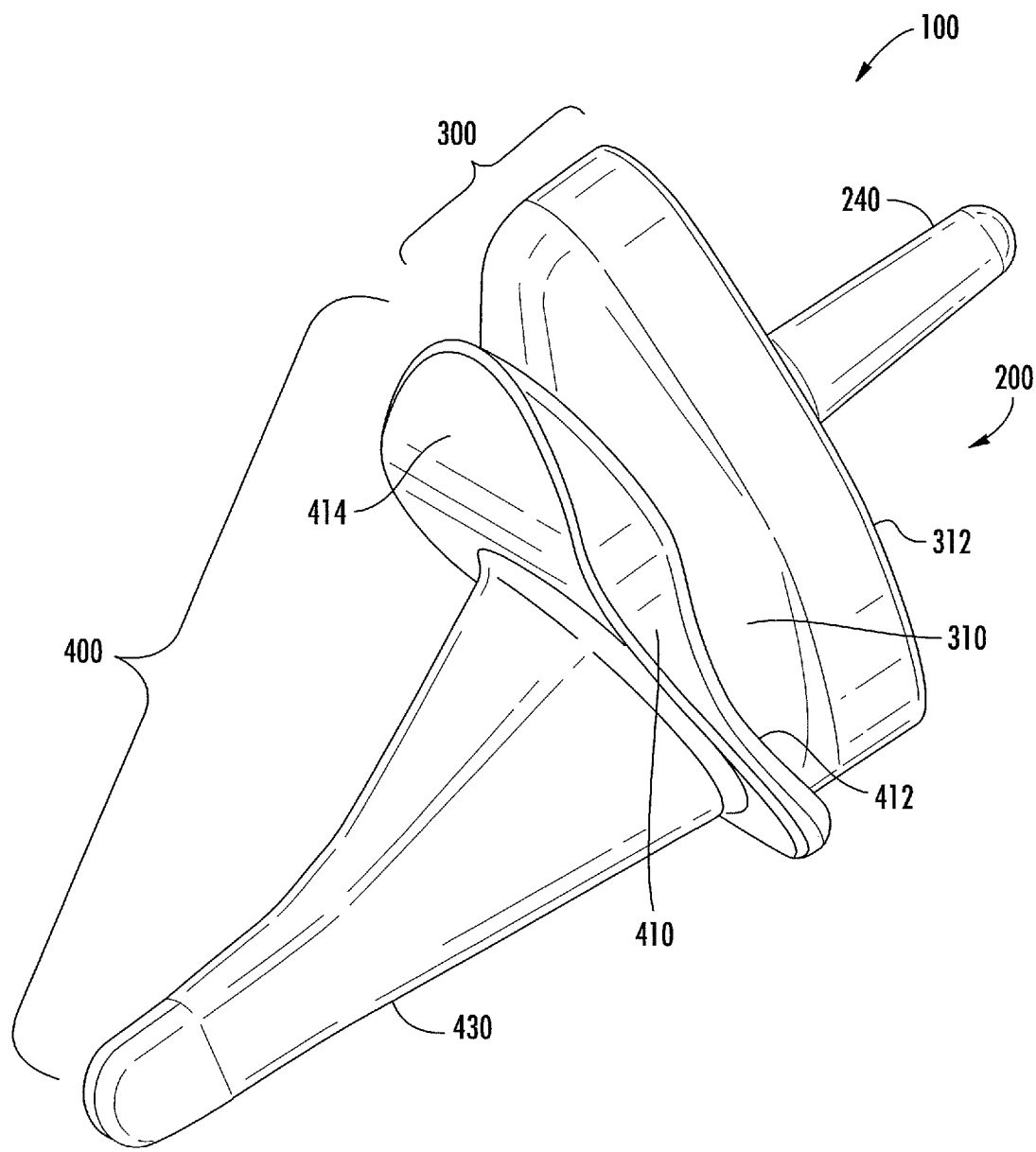
Figure 25:
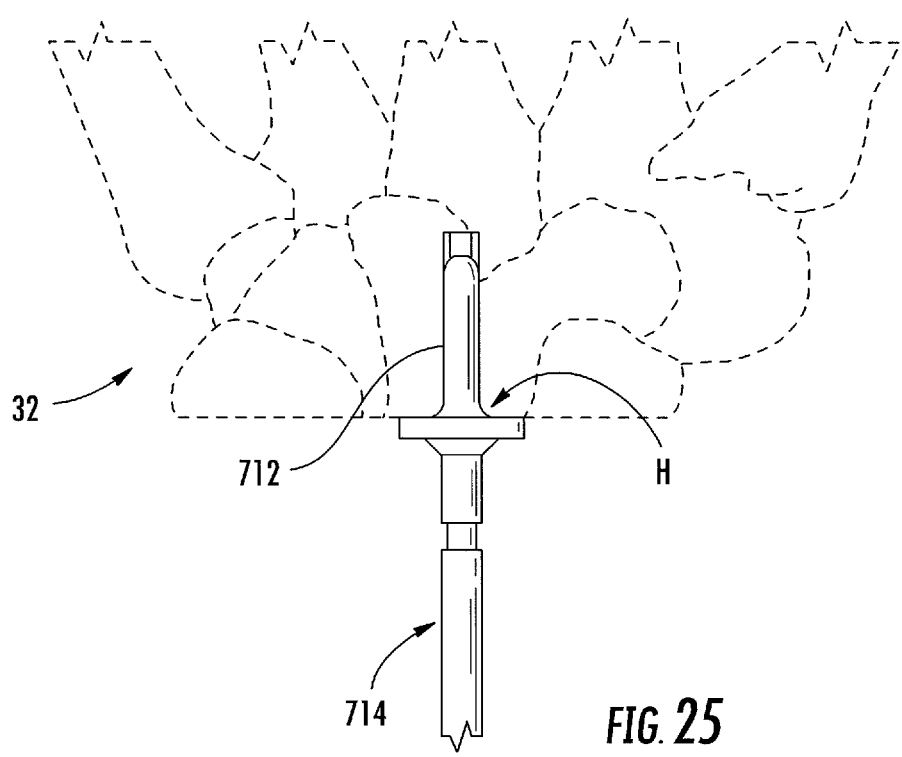
Figure 26:
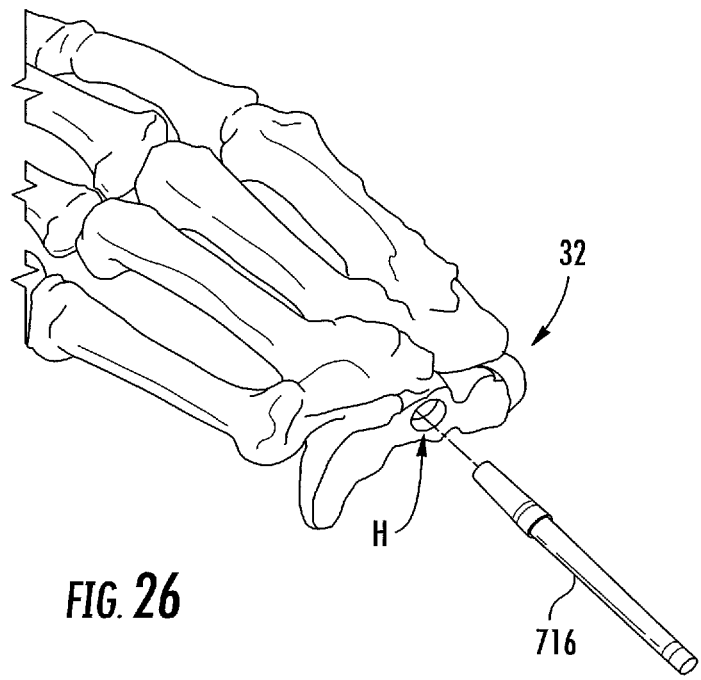

A small, oscillating saw blade (not shown) can be used to make the carpal cut. To complete the cut, resection guide 702 may need to be removed, but K-wires 710 may need to be retained. As shown in FIG. 25, an appropriate sized tip 712 of a starter carpal reamer designated 714 can be inserted into the 3.5 mm drill hole H (FIG. 24) and can be used to create a tapered cut or channel configured to match the geometry of carpal post 240 (FIG. 2). As FIG. 26 illustrates, tip 712 of reamer 714 can be removed from hole H, and a capitate cement broach 716 can be inserted into reamed hole H and used to widen the diameter of hole H to create room for a thin mantle of bone cement (not shown) disposed about or around a portion of carpal post 240 (FIG. 2) of carpal implant component 200 (FIG. 2). Capitate cement broach 716 can be removed.

Figure 27:
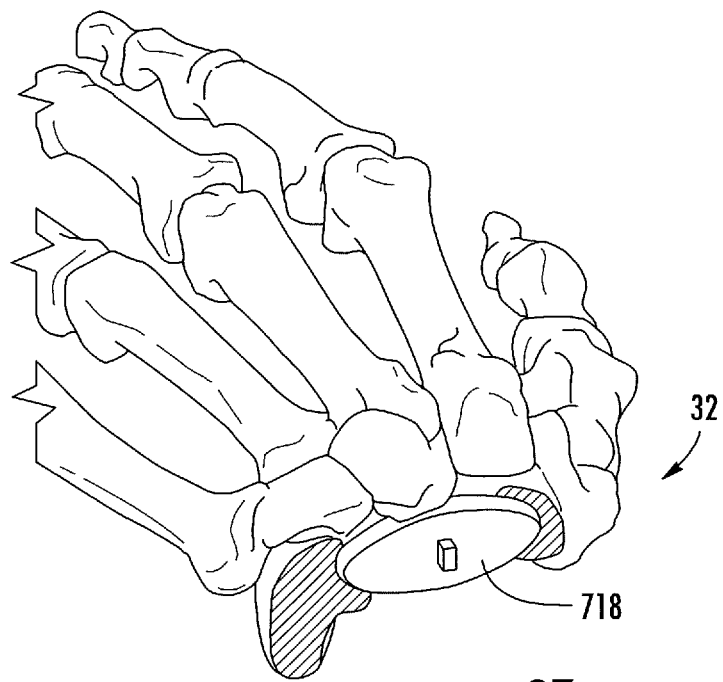
Figure 28:
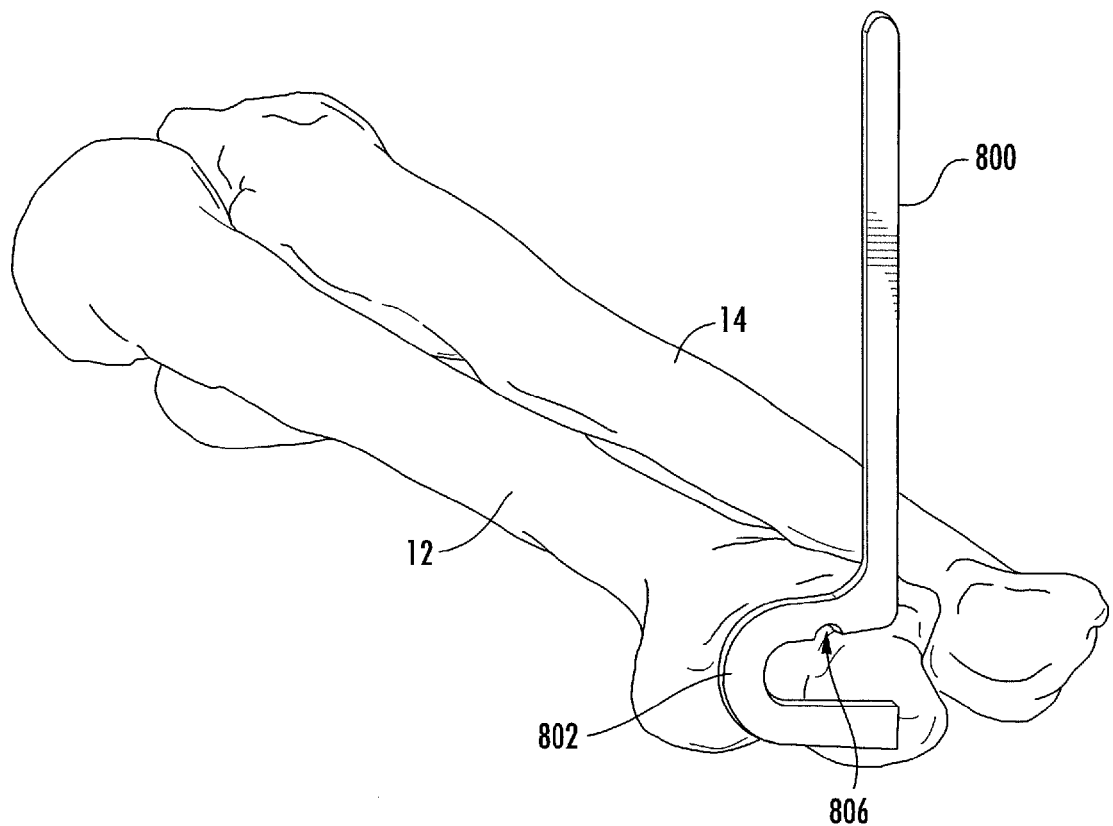
Figure 29A:
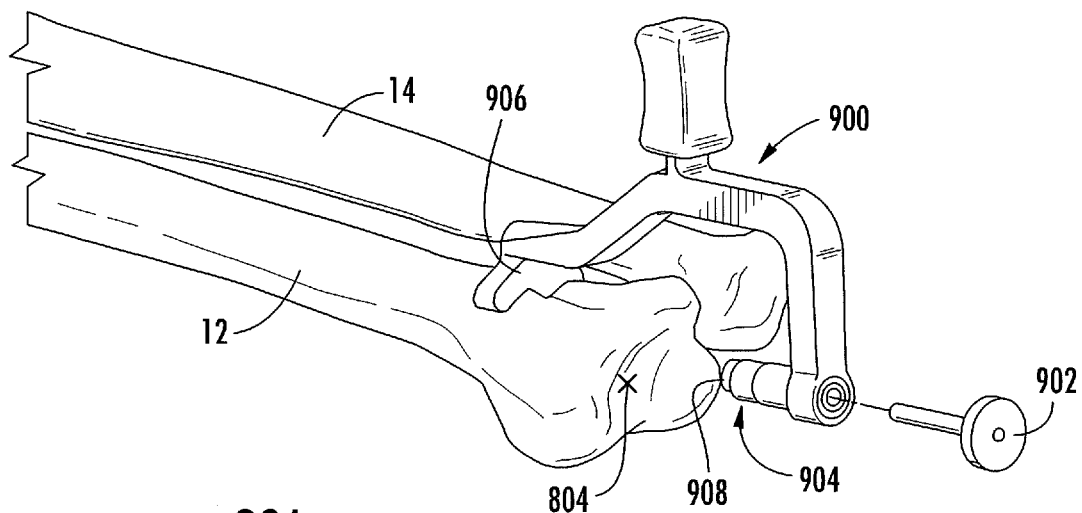
Figure 29B:
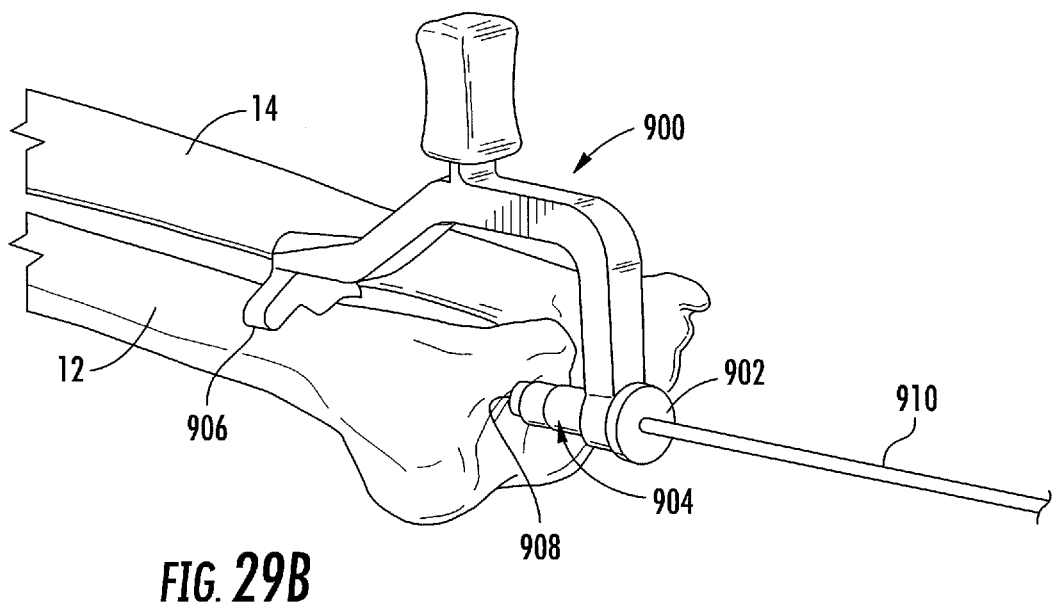

As FIG. 27 illustrates, a trial carpal implant component 718 can be inserted into capitate hole (e.g., hole H) with use of a carpal plate impactor (not shown). A mallet can be used to strike impactor, thus impacting trial carpal implant 718 into place.

Preparation of Radius

FIGS. 28 to 38 illustrate preparation of a radius bone 12 for receiving radial implant component 400 (FIG. 2). A radial template 800 of a selected size is used to show a projected outline of radial implant component 400 (FIG. 2) on a surface of the radius 12. After aligning a radial edge 802 of template 800 with a lateral edge of radius 12, a small mark generally designated 804 (FIG. 29A) can be made on surface of radius 12 at a location of a notch or hole 806 of template 800. FIGS. 29A and 29B illustrate a modular K-wire guide or drill guide, generally designated 900. A K-wire sleeve 902 can be inserted into a modular K-wire guide barrel generally designated 904. A saddle 906 of modular drill guide 900 can be placed on a portion of radius 12, and an arbor pipe 908 can be aligned with mark 804 on a portion of radial surface. A 1.4 mm K-wire 910 can be drilled through drill guide 900 and into radius 12. K-wire sleeve 902 and drill guide 900 can then be sequentially removed.

Figure 30A:
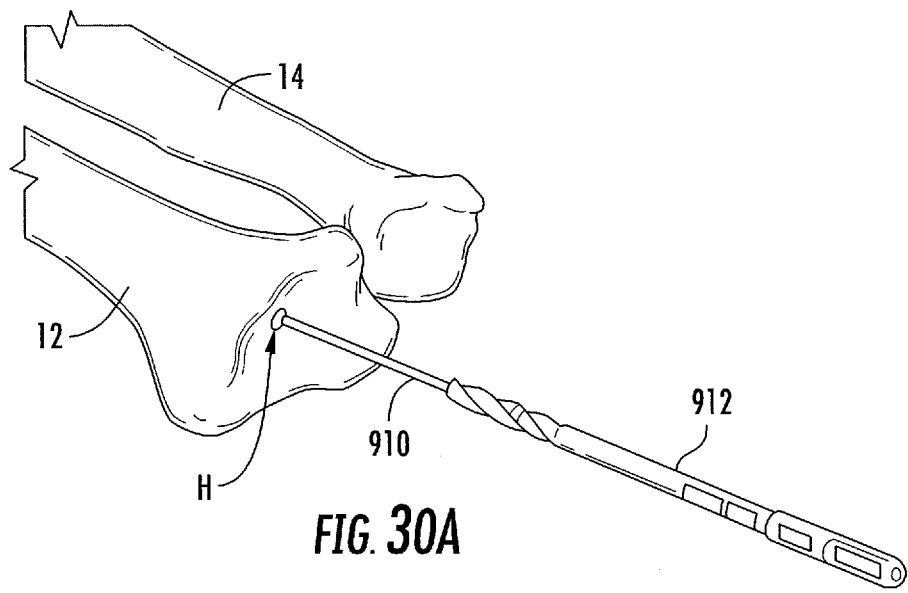
Figure 30B:
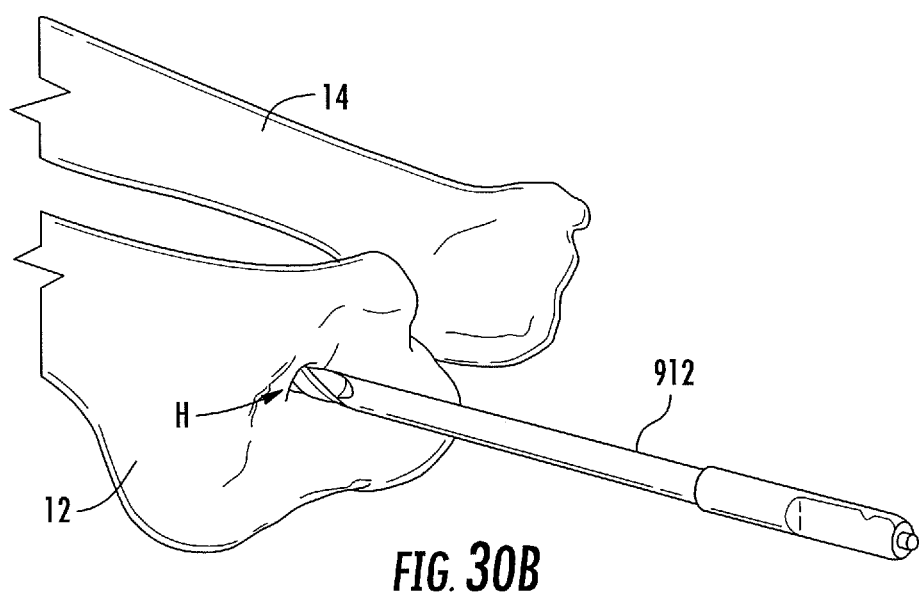
Figure 31:
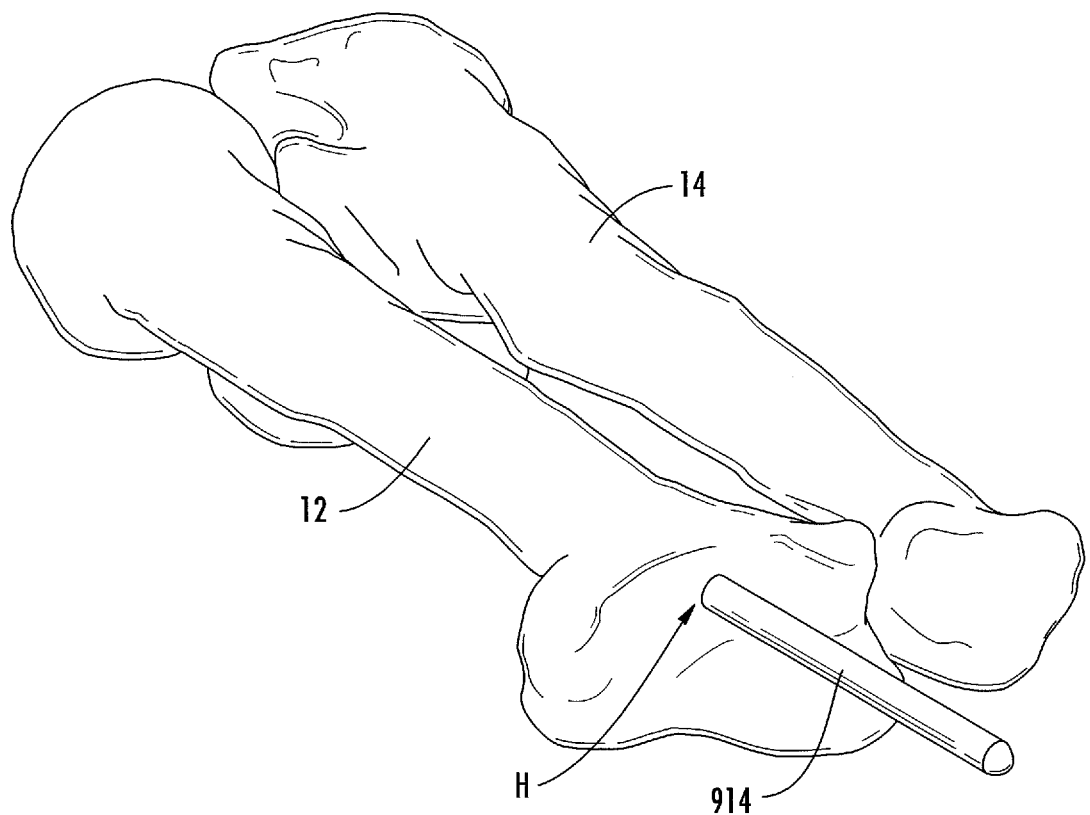

As FIGS. 30A and 30B illustrate, a 3.5 mm cannulated drill bit 912 can be used to drill a hole H over K-wire 910 into a medullary canal portion of radius 12. As FIG. 31 illustrates, a radial alignment guide rod 914 can be inserted in hole H and advanced far into the medullary canal. Rod 914 can be configured to slide easily without bending. Fluoroscopy can be used to confirm that alignment guide rod 914 is centered or substantially centered within canal or hole H.

Figure 32:
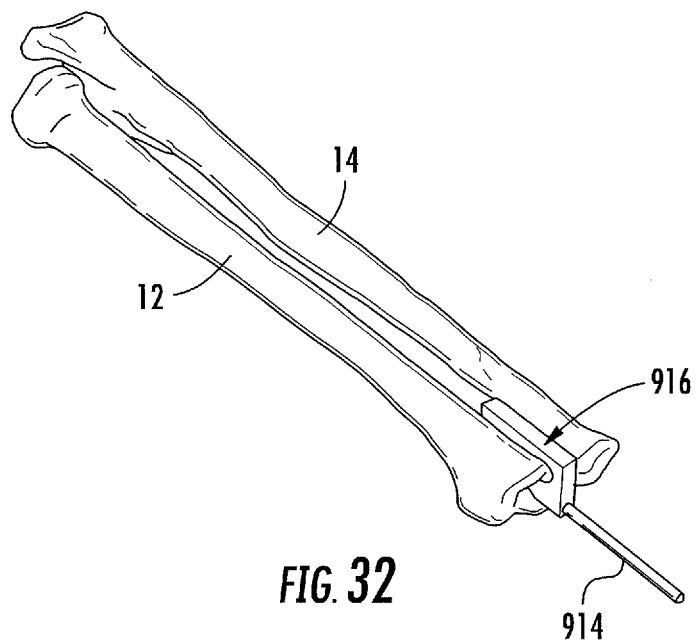
Figure 33A:
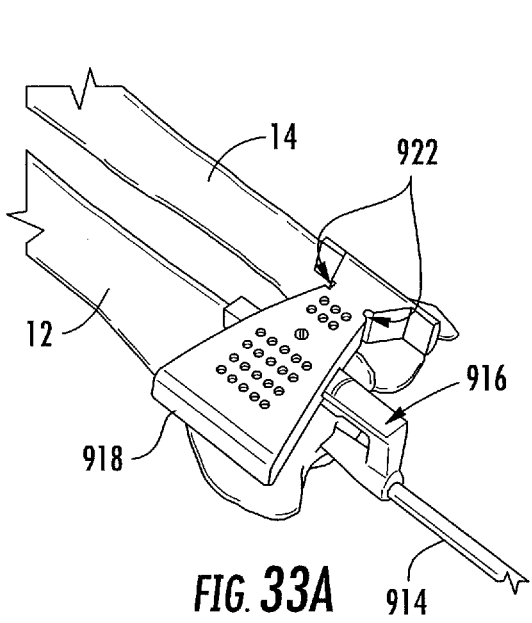
Figure 33B:
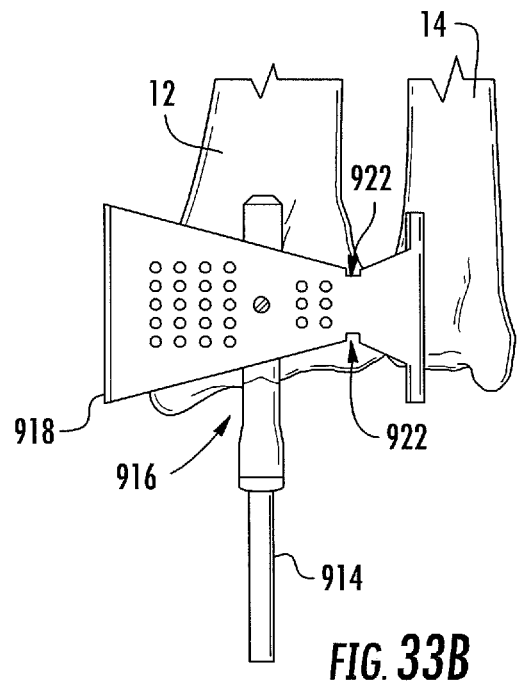

As FIG. 32 illustrates, a radial guide bar generally designated 916 can be slid over alignment guide rod 914 until it contacts a portion of radius 12. FIGS. 33A and 34B illustrate a radial resection guide 918 of a selected size mounted onto guide bar 916 and slid into proper position. Neutral lines on guide bar 916 can indicate a position of resection guide 918 that would result in resection on a plane tangent to an articular surface of radius 12. The amount of resection desired can then be precisely gauged, aiming for just beneath the articular surface of radius 12. Resection guide 918 can further comprise one or more grooves 922 for positioning a radial score guide.

Figure 34A:
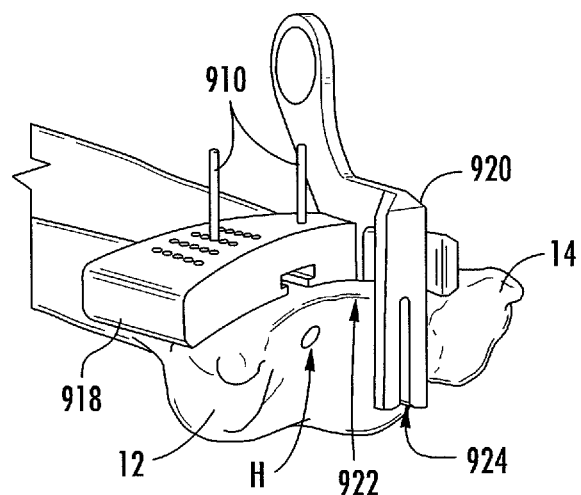
Figure 34B:
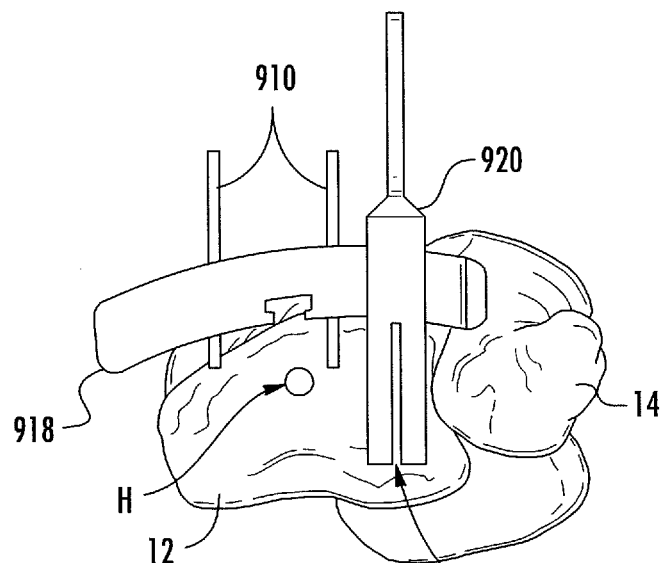

FIG. 34A illustrates that while resection guide 918 can be held aligned with a dorsal surface of the radius 12, two or three 1.4 mm K-wires 910 can be inserted through holes in resection guide 918 and drilled into a distal portion of radius 12. A radial side of resection guide 918 can have five rows of four or five holes, depending on size, as well as a separate three rows of two or three holes on an ulnar side of guide 918. By using the middle holes in the rows, resection guide 918 can be adjusted proximally or distally if necessary.

As FIGS. 34A and 34B further illustrate alignment guide rod 914 and guide bar 916 can be removed and resection guide 918 can be slid down against a portion of radius 12. Lister's tubercle may need to be removed to fully seat resection guide 918 against a portion of radius 12. K-wires 910 can be cut above resection guide 918. The position of resection guide 910 can be checked for proper level of resection and adjusted if needed. A radial score guide 920 can then be slid into grooves 922 (FIG. 33B) on proximal and distal sides of resection guide 918 until it is fully seated on a surface of resection guide. A small, oscillating saw blade (not shown) can be used to score a portion of radius 12 through a slot 924 in a portion of radial score guide 920 as illustrated in FIG. 34B, for marking where the radial cut should end in order to protect the DRUJ. Radial score guide 920 can be removed, and the oscillating saw blade can be used to make a radial cut. To complete the cut through the volar cortex, resection guide 918 may need to be removed. Resection guide 918 and K-wires 910 can then be removed. If a large osteophyte remains on the volar rim of a distal portion of radius 12, it should also be resected.

Figure 35:
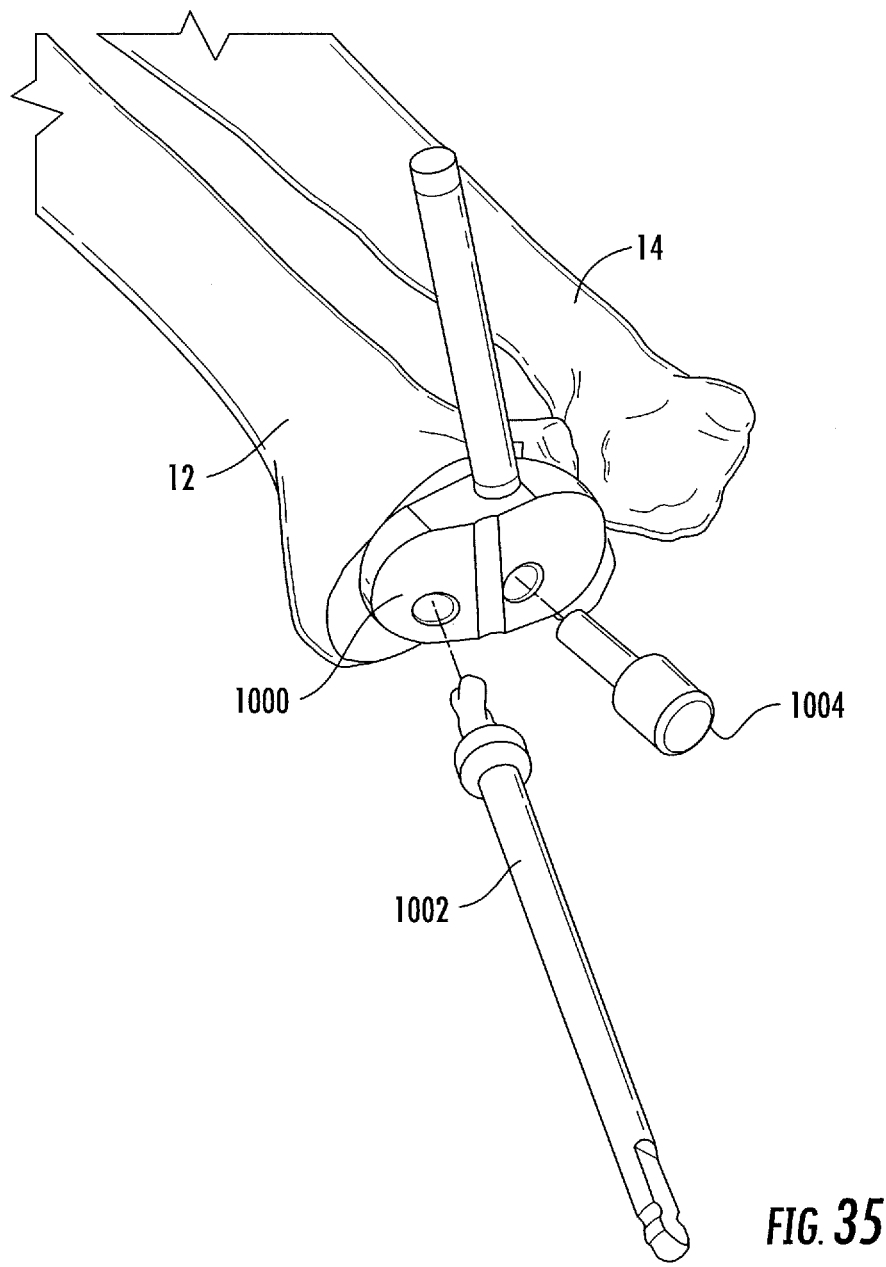

Referring to FIG. 35, a post (obstructed from view) of a radial drill guide 1000 can be inserted into medullary canal or hole H of radius 12. A 4.0 mm stop drill bit 1002 can be used to drill two shallow holes in the volar-radial and volar-ulnar corners of radius 12 where portions of stem 430 (FIG. 2) of radial implant component 400 (FIG. 2) can be embedded. After drilling a first hole, a radial drill guide peg 1004 can be inserted through drill guide 1000 into the hole to prevent rotation of drill guide 1000 while drilling the second hole with bit 1002. Radial drill guide 1000 and peg 1004 can be removed, and an alignment rod (e.g., 914 FIGS. 31-33B) can be reinserted into medullary canal or hole H. A punch (not shown) can be inserted into a broach handle and slid over alignment rod until it contacts radius 12. A mallet can be used to drive punch into radius 12. The punch and alignment rod can be removed and a plug of cut bone can be removed from hole H.

As FIGS. 36A to 36C illustrate, a proper size broach generally designated 1006 can comprise a tip portion 1008 configured for insertion into a broach handle 1010. A nose portion 1012 of broach 1006 can be placed into hole H in radial surface of radius 12 with its sides aligned substantially parallel to the sigmoid notch and volar rim of radius 12. Using a mallet, the broach can be driven into the distal radius 12 until a tray portion 1014 contacts the resected surface. Broach 1006 can be removed.

Figure 37:
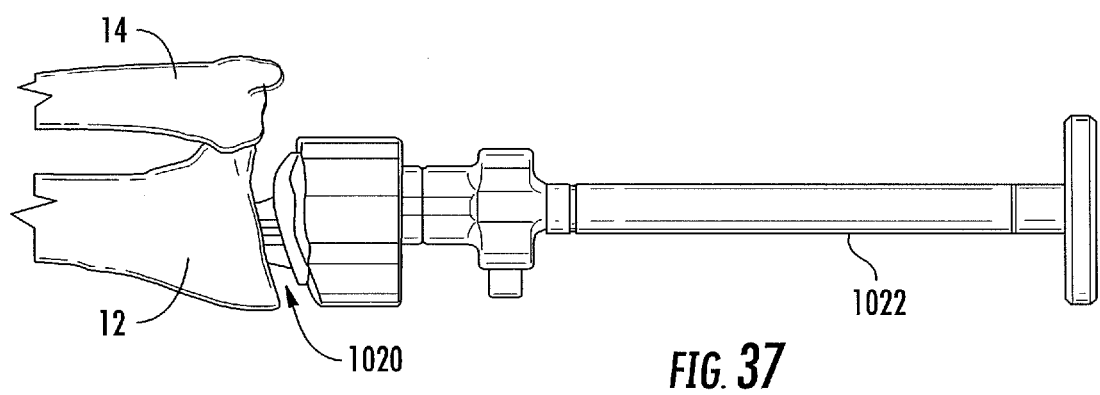
Figure 38:
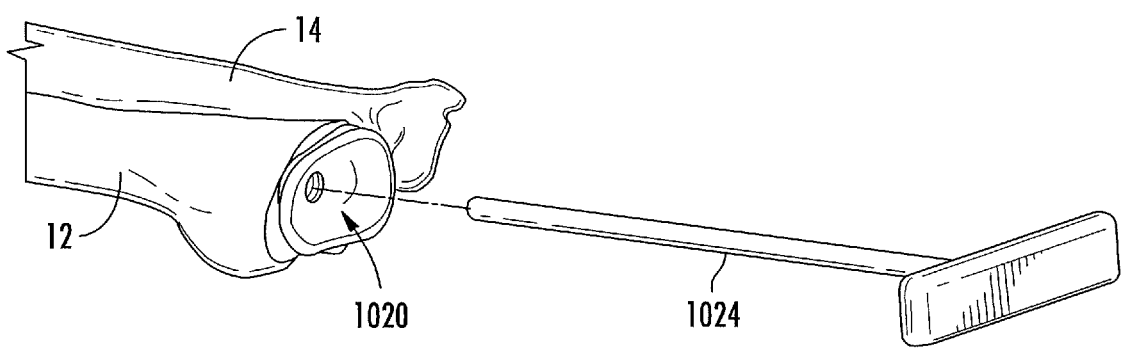

According to FIG. 37, a trial radial component designated 1020 can be inserted into the broached hole of radius 12 using a radial impactor 1022. Care should be taken during insertion of trial component 1020 to maintain proper alignment within the prepared metaphysis. FIG. 38 illustrates an extractor tool (T-handle) 1024 which can be used and applied to trial radial component 1020 for removal thereof.

Trial Reduction

Figure 39:
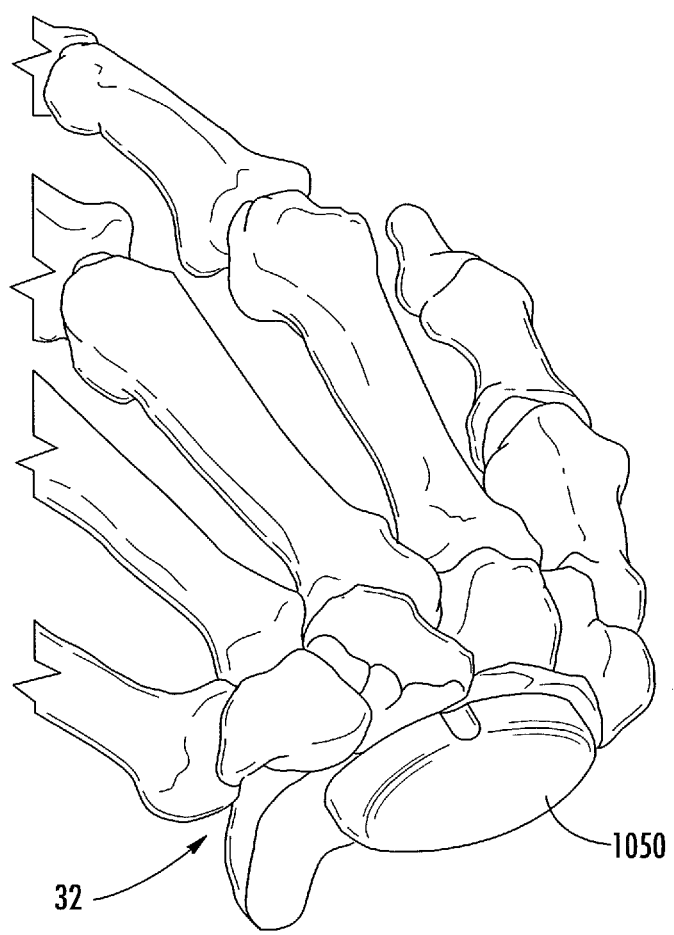

If removed, radial trial implant component 1020 can be reinserted. As FIG. 39 illustrates, a trial bearing component or bearing member 1050, for example comprising polyethylene of a standard thickness of appropriate size can be attached to trial carpal implant (718, FIG. 27). The prosthesis, including trial components, can be reduced and range of motion and stability can be checked. The prosthesis should be stable and should demonstrate approximately 35° of flexion and approximately 35° of extension with modest tightness at full extension. If the volar capsule is tight and limiting extension, radius 12 may need to be shortened, for example, by a couple of millimeters. Caution should be exercised to avoid excessive shortening. If a severe preoperative flexion contracture is present, a step-cut tendon lengthening of the flexor carpi ulnaris and occasionally the flexor carpi radialis can be required to achieve proper balance and motion. When volar instability is present, the volar capsule can be inspected and, if detached, it can be repaired to a rim of distal radius. If the volar capsule is intact, a thicker trial polyethylene component can be required to increase soft tissue tension and joint stability. A mild dorsal instability should respond to capsule closure but a thicker polyethylene can be considered for marked instability.

Implantation

Figure 40:
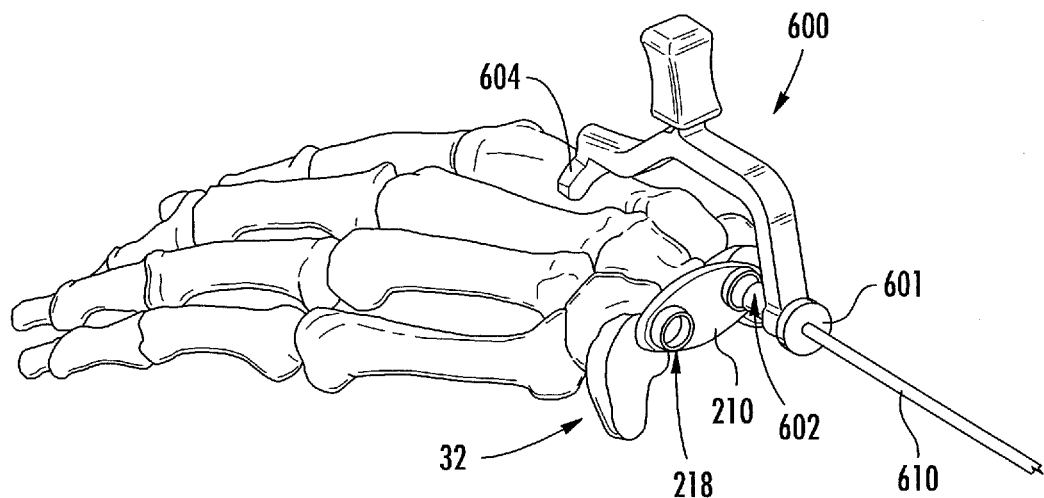

The trial components (e.g., 716 in FIG. 27, 1020 in FIGS. 38, and 1050 in FIG. 39) should be removed and the wound should be thoroughly irrigated. Three horizontal mattress sutures such as 2-0 polyester can be placed through small bone holes along the dorsal rim of distal radius 12 for later capsule closure. If the ulnar head (e.g., 500, FIG. 19) was resected, sutures should also be placed through its dorsal neck. When indicated by the surgeon, bone cement can be prepared in the usual manner and injected into cavities, or holes H adapted to receive each of the carpal post 240 and radial stem 430 just prior to final implantation. According to FIG. 40, a carpal impactor (not shown) has been used to drive carpal plate 210 into capitate hole (e.g., hole H, FIG. 26)

while maintaining proper position. K-wire sleeve 601 can be inserted into barrel portion 602 of modular K-wire guide 600. Modular K-wire guide 600 can be applied with its barrel portion 602 in a radial hole or aperture 218 of carpal implant component 200 and its saddle portion 604 on the second metacarpal shaft over the skin. A 1.4 mm K-wire 610 can be drilled through the scaphoid, trapezoid, and into the second metacarpal shaft. Guide wire 610 may or may not be substantially perpendicular to carpal implant component 200. Carpal implant component 200, apertures 218, and screw heads 230 (FIG. 5) are designed to accommodate screw insertions at oblique angles. K-wire sleeve 601 and K-wire guide 600 can be removed sequentially.

Figure 41A:
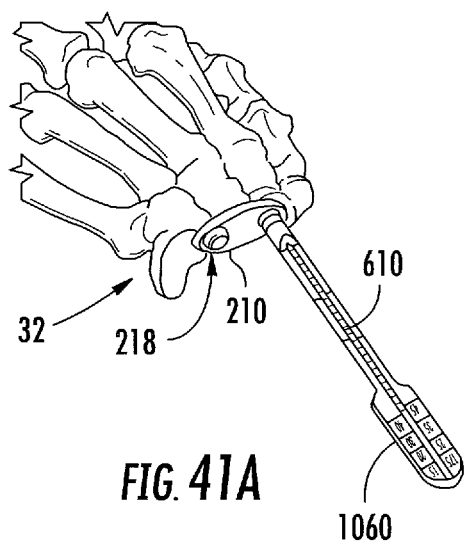
Figure 41B:
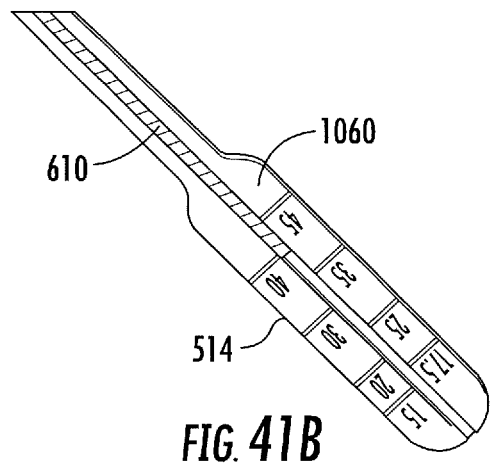
Figure 42:
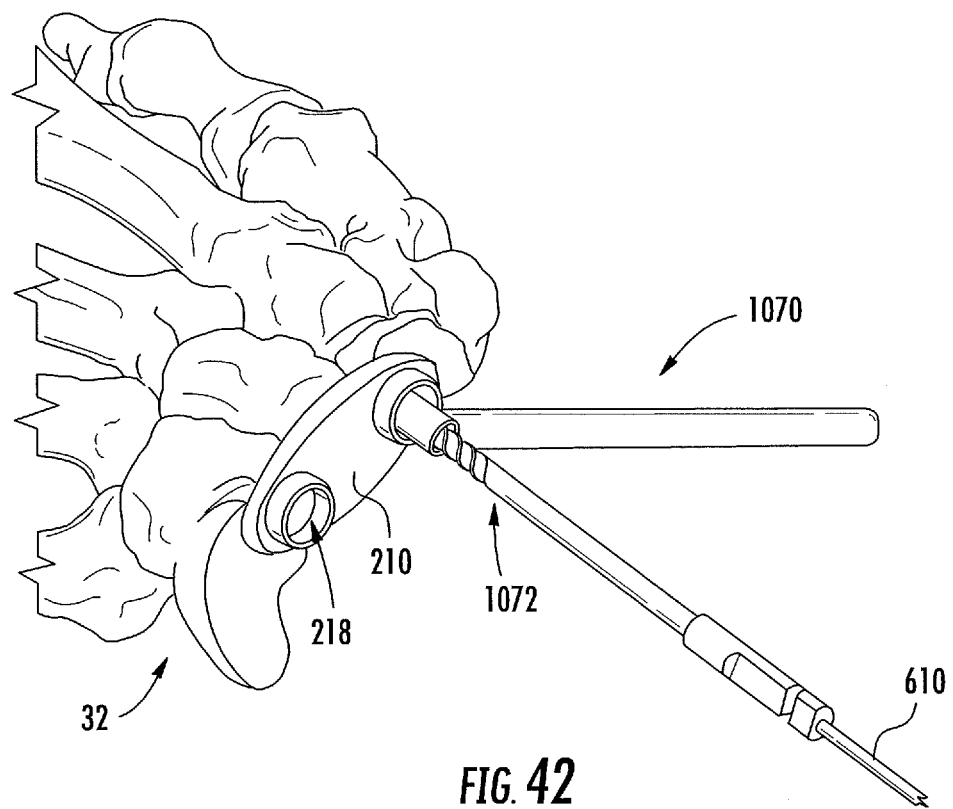
Figure 43:
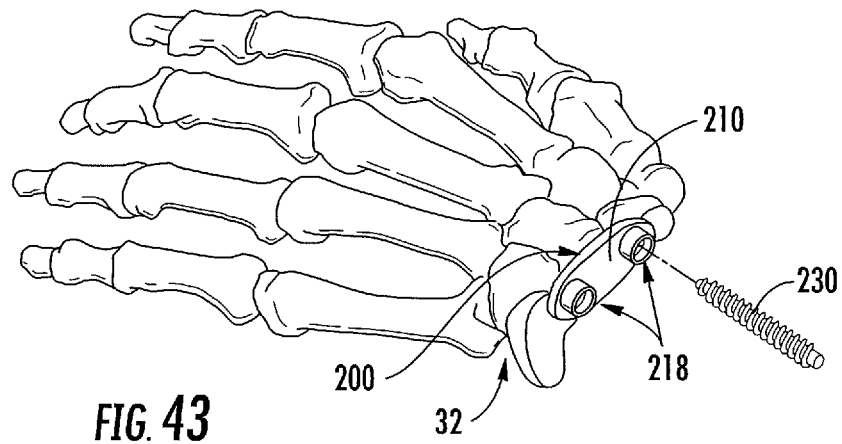
Figure 44:
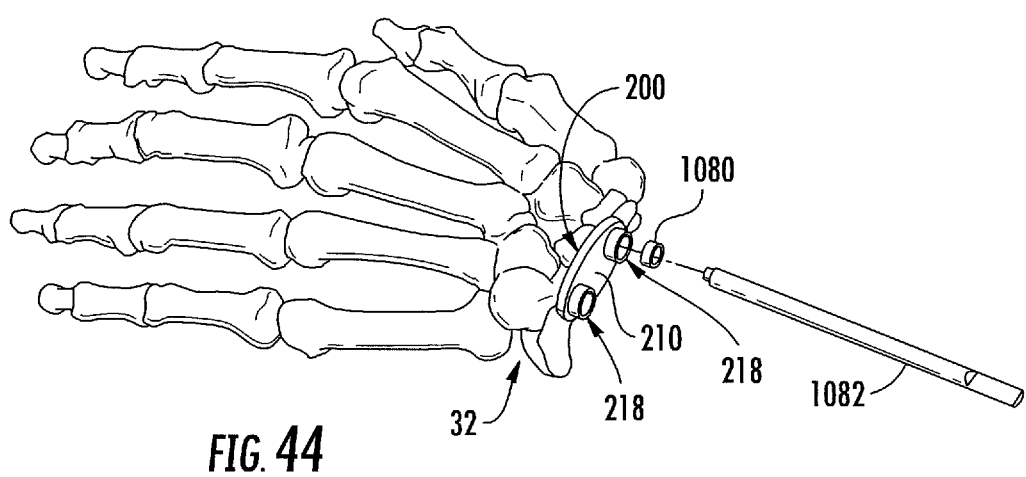

According to FIGS. 41A and 41B, a K-wire depth gauge 1060 can be slid over K-wire 610 to contact an interior of a carpal component hole. A depth of K-wire 610 insertion can be read from gauge 1060 in FIG. 41B, and the gauge 1060 can be subsequently removed. As shown in FIG. 42, a thread protective drill sleeve designated 1070 can be inserted into a radial hole, or aperture 218 of carpal plate 210, and a 2.5 mm cannulated drill bit 1072 can be used to drill over K-wire 610 to the depth of K-wire insertion using depth markings (not shown) on drill bit 1072. Referring to FIG. 43, a 4.5 mm self-tapping screw 230 (also FIG. 5) can be inserted within aperture 218 and tightened firmly. Referring to FIG. 44, a screw locking cap 1080 can be threaded into aperture 218 in carpal plate 210 and tightened firmly to lock screw 230 into place thereby securing a portion of carpal implant component 200 to portions of wrist or carpal complex bones.

A similar technique can be used for an ulnar hole (e.g., remaining aperture 218) of carpal plate 210, with a few differences. Saddle portion 604 of drill guide 600 (FIG. 40) can be placed on the fourth metacarpal shaft over the skin. The mobile fourth metacarpal can be held elevated (fourth carpometacarpal (CMC) extended) while drilling in K-wire 610 to ensure hole or aperture 218 is not directed volarly. K-wire 610 can be drilled through a portion of the hamate, but does not cross the mobile fourth CMC joint. The insertion depth of K-wire 610 can be checked with K-wire depth gauge 1060 (FIGS. 41A and 41B) and a 2.5 mm cannulated drill bit 1070 (FIG. 42) can be used to drill a hole over K-wire 610 to the K-wire insertion depth. A 4.5 mm self-tapping screw 230 (FIG. 43) can be inserted and tightened firmly, and a locking cap 1080 (FIG. 44) can be inserted and tightened firmly via tightening tool 1082. Any remaining K-wires 610 can be removed from the carpus and a radial impactor can be used to drive radial implant component 400 into the metaphysis with care to maintain proper alignment.

Figure 45:
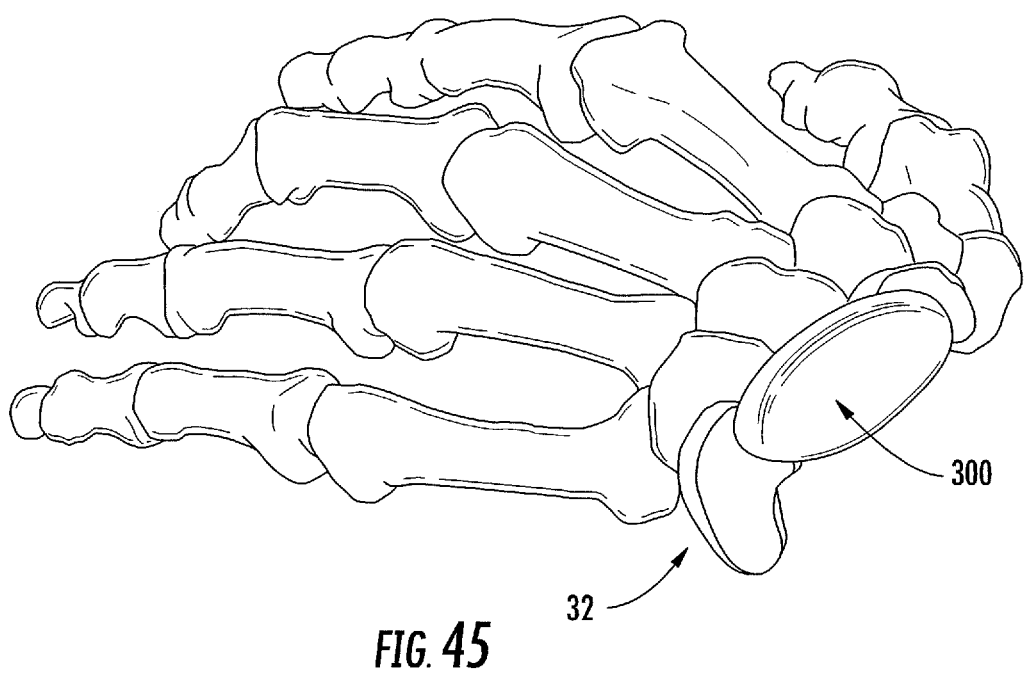

As an optional step, a trial polyethylene bearing member 1050 (FIG. 39) can be used to confirm the proper size for joint motion and stability prior to provision of an actual bearing member 300. According to FIG. 45, an impactor has been used to snap, for example, a polyethylene bearing member 300 onto carpal plate 210 with firm mallet taps. It should be confirmed that polyethylene bearing member 300 is completely engaged onto carpal plate 210. Prosthesis 100 can be reduced, and a final assessment of wrist motion, balance and stability can be performed.

Closure

The intercarpal articular surfaces of the triquetrum, hamate, capitate, scaphoid and trapezoid can be removed using a curette or burr (e.g., avoiding carpal component fixation screws 230). Cancellous chips from previously resected bone can be packed into the spaces. The dorsal capsule can be reattached to the distal margin of radius using the previously placed sutures. The capsule can be re-approximated at the distal radioulnar joint or attached to the ulnar neck using the previously placed sutures if the head was resected. The medial and lateral aspects of the capsule can also be closed. If the capsule is insufficient for closure with the wrist flexed, the extensor retinaculum can be divided in line with its fibers and one half can be placed under the tendons to augment the capsule.

The entire prosthesis (e.g., 100) can be covered to achieve its proper stability and function and to avoid extensor tendon irritation. The remaining extensor retinaculum can be repaired over the tendons to prevent bowstringing; however, the extensor pollicis longus (EPL), tensor carpi radialis brevis (ECRB) and extensor carpi radialis longus (ECRL) can typically be left superficial to the retinaculum. If necessary to maintain the extensor carpi ulnaris (ECU) dorsally over ulna, a separate sling can be made from the retinaculum. A suction drain can be placed and the skin is closed in layers. A bulky gauze dressing and a short arm plaster splint can be applied.

Post-Operative Management

Strict elevation and early passive and active digital motion are encouraged to reduce swelling. At approximately ten days, the sutures can be removed and an x-ray can be obtained to confirm prosthetic reduction. A removable wrist splint can be fabricated and used when not performing exercises. Gentle wrist exercises can be started, including active flexion and extension, radial and ulnar deviation, and pronation and supination. A therapist can be engaged to ensure progress. The splint may be discontinued at the fourth postoperative week and hand use advanced. The exercise program should be continued and strengthening can be added. Power grip and lifting is discouraged for the first eight weeks. A dynamic splint may occasionally be used if recovery of motion is difficult or incomplete. The patient is advised against impact loading of the wrist and repetitive forceful use of the hand.

Embodiments of the present disclosure shown in the drawings and described above are exemplary of numerous embodiments that can be made within the scope of the appending claims. It is contemplated that the implant components, systems, and related methods can comprise numerous configurations other than those specifically disclosed.

What is claimed is:

1. A prosthetic wrist implant comprising:
   a radial implant component comprising a tray having a distal bearing surface and a proximal surface having an elongated radial stem extending therefrom adapted for attachment to a radius bone, the tray comprising radial and ulnar sides and volar and dorsal sides; and
   wherein the distal bearing surface of the radial implant component comprises a flexion/extension radius of curvature that increases along the radial/ulnar direction.

2. The prosthetic wrist implant of claim 1, wherein the flexion/extension radius of curvature on the ulnar side is larger than the flexion/extension radius of curvature on the radial side.

3. The prosthetic wrist implant of claim 1, wherein the flexion/extension radius of curvature increases from the radial side to the ulnar side.

4. The prosthetic wrist implant of claim 1, wherein a radial/ulnar deviation radius of curvature is constant.

5. The prosthetic wrist implant of claim 1, wherein the tray is wider on the ulnar side than the radial side.

6. The prosthetic wrist implant of claim 1, wherein the width of the tray generally increases from the radial side to the ulnar side.

7. The prosthetic wrist implant of claim 1, wherein the radial stem is non-circular and has a central plane that bisects the stem along an elongated length thereof, and wherein the radial tray comprises a central plane that bisects the radial tray between the volar and dorsal sides, and wherein the central plane of the radial tray is acutely angled with respect to the central plane of the radial stem.

8. The prosthetic wrist implant of claim 7, wherein the central plane of the radial tray is acutely angled with respect to the central plane of the radial stem by about 3° to about 20°.

9. The prosthetic wrist implant of claim 1, further comprising a carpal implant component comprising a carpal plate having a distal surface adapted for attachment to one or more carpal bones, and a proximal surface coupled with a bearing member, the bearing member having a proximal bearing surface for articulation with the distal bearing surface of the radial component.

10. A prosthetic wrist implant comprising:

a radial implant component comprising a radial tray and an elongated radial stem, the radial tray having a distal bearing surface and a proximal surface, wherein the elongated radial stem extends from the proximal surface for fixation to a radius bone, the radial tray having radial and ulnar sides and volar and dorsal sides; and wherein the radial stem is non-circular and has a central plane that bisects the stem along an elongated length thereof, and wherein the radial tray comprises a central plane that bisects the radial tray between the volar and dorsal sides, and wherein the central plane of the radial tray is acutely angled with respect to the central axis plane of the radial stem.

11. The prosthetic wrist implant of claim 10, wherein the central plane of the radial tray is acutely angled with respect to the central plane of the radial stem by about 3° to about 20°.

12. The prosthetic wrist implant of claim 10, further comprising a carpal implant component comprising a carpal plate having a distal surface adapted for attachment to one or more carpal bones, and a proximal surface coupled with a bearing member, the bearing member having a proximal bearing surface for articulation with the distal bearing surface of the radial component.

\* \* \* \* \*